United States Patent
Badal-Soler

(10) Patent No.: US 10,722,190 B2
(45) Date of Patent: Jul. 28, 2020

(54) ADAPTIVE X-RAY FILTER USING SPATIAL EXPOSURE TIME MODULATION WITH DYNAMIC COLLIMATORS

(71) Applicant: The United States of America, as represented by the Secretary, Department of Health and Human Services, Bethesda, MD (US)

(72) Inventor: Andreu Badal-Soler, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 222 days.

(21) Appl. No.: 15/751,119

(22) PCT Filed: Aug. 8, 2016

(86) PCT No.: PCT/US2016/045987
§ 371 (c)(1),
(2) Date: Feb. 7, 2018

(87) PCT Pub. No.: WO2017/027452
PCT Pub. Date: Feb. 16, 2017

(65) Prior Publication Data
US 2018/0228452 A1    Aug. 16, 2018

Related U.S. Application Data

(60) Provisional application No. 62/202,390, filed on Aug. 7, 2015.

(51) Int. Cl.
*A61B 6/06* (2006.01)
*A61B 6/03* (2006.01)
(Continued)

(52) U.S. Cl.
CPC ................ *A61B 6/06* (2013.01); *A61B 6/032* (2013.01); *A61B 6/4035* (2013.01); *A61B 6/544* (2013.01);
(Continued)

(58) Field of Classification Search
CPC ......... A61B 6/032; A61B 6/06; A61B 6/4035; A61B 6/502; A61B 6/544; A61B 6/582; G21K 1/025; G21K 1/043; G21K 1/10
See application file for complete search history.

(56) References Cited

U.S. PATENT DOCUMENTS

| 5,164,976 A | 11/1992 | Scheid et al. |
| 2005/0094762 A1 | 5/2005 | Dunham et al. |

(Continued)

OTHER PUBLICATIONS

International Search Report and Written Opinion for related International Application No. PCT/US2016/045987, dated Oct. 14, 2016, 12 pages.

*Primary Examiner* — Mark R Gaworecki
(74) *Attorney, Agent, or Firm* — Klarquist Sparkman, LLP

(57) ABSTRACT

Disclosed herein are adaptive filters, radiographic systems, and methods for controlling the radiation exposure of a target object during a radiographic imaging procedure. An adaptive filter can comprise first and second dynamic collimators that block or attenuate radiation that is incident upon the collimators, but allow radiation to pass between the collimators to reach the target object and radiation detector. The collimators can move relative to each other during a radiation emission such that the motion of the collimators allows different amounts of radiation from the radiation source to pass between the two collimators to each portion of the target object during the radiation emission. The amounts of radiation allowed to reach each portion of the (Continued)

target object can be determined based on a thickness of each portion of the target object.

22 Claims, 20 Drawing Sheets

(51) Int. Cl.
    *A61B 6/00*           (2006.01)
    *G21K 1/04*           (2006.01)
    *G21K 1/02*           (2006.01)
    *G21K 1/10*           (2006.01)

(52) U.S. Cl.
    CPC ............. *G21K 1/025* (2013.01); *G21K 1/043* (2013.01); *G21K 1/10* (2013.01); *A61B 6/502* (2013.01); *A61B 6/582* (2013.01)

(56) References Cited

U.S. PATENT DOCUMENTS

2012/0128120 A1     5/2012   De Man et al.
2013/0343512 A1   12/2013   Heuscher et al.
2015/0131781 A1     5/2015   Ohashi et al.

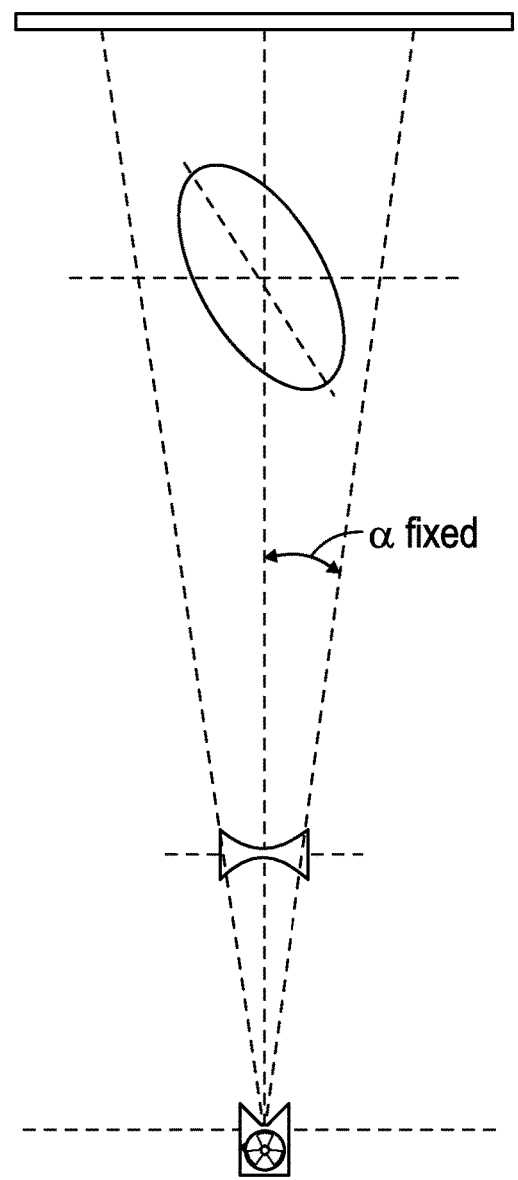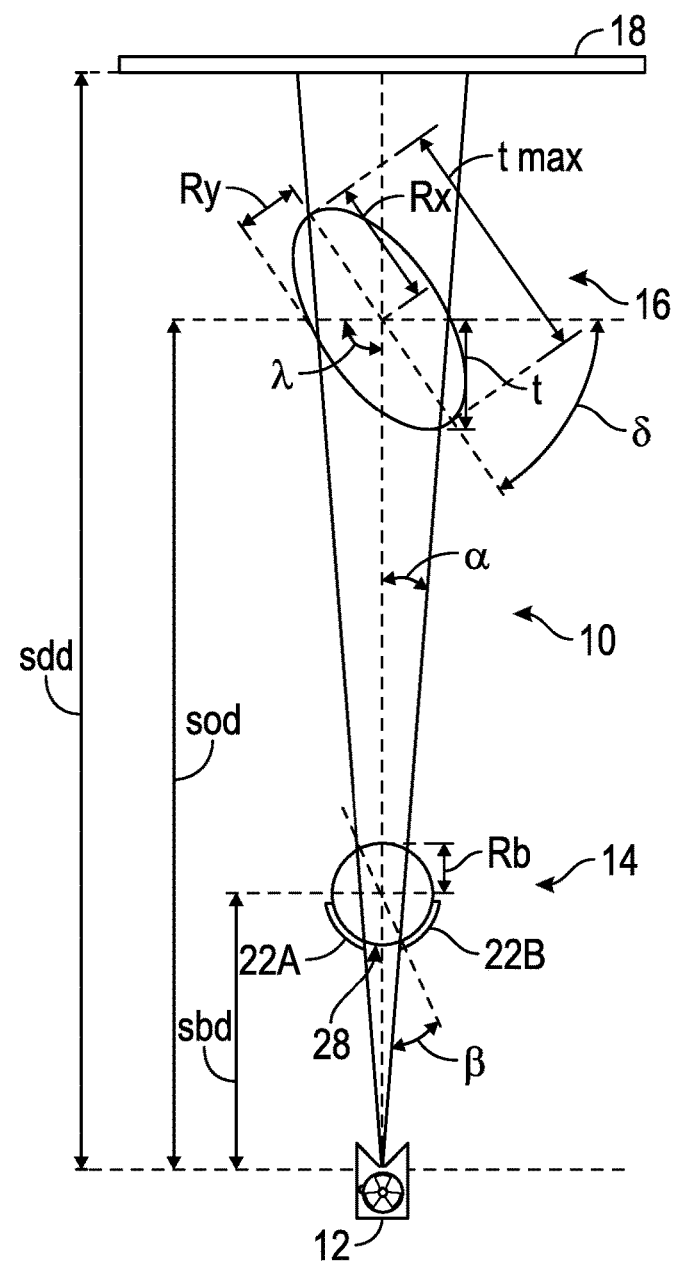
FIG. 1A
FIG. 1B

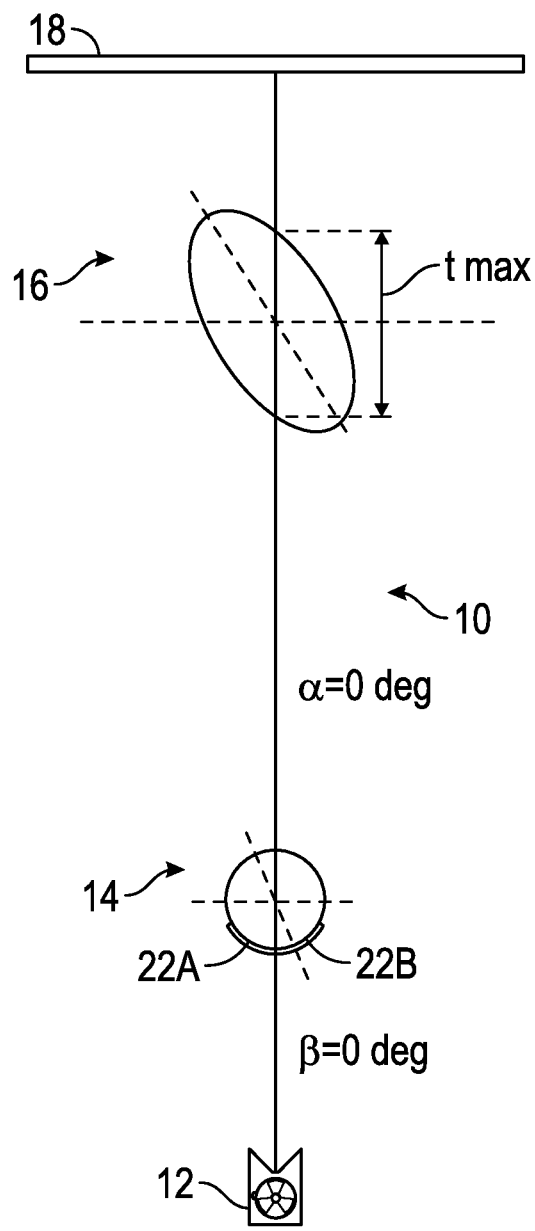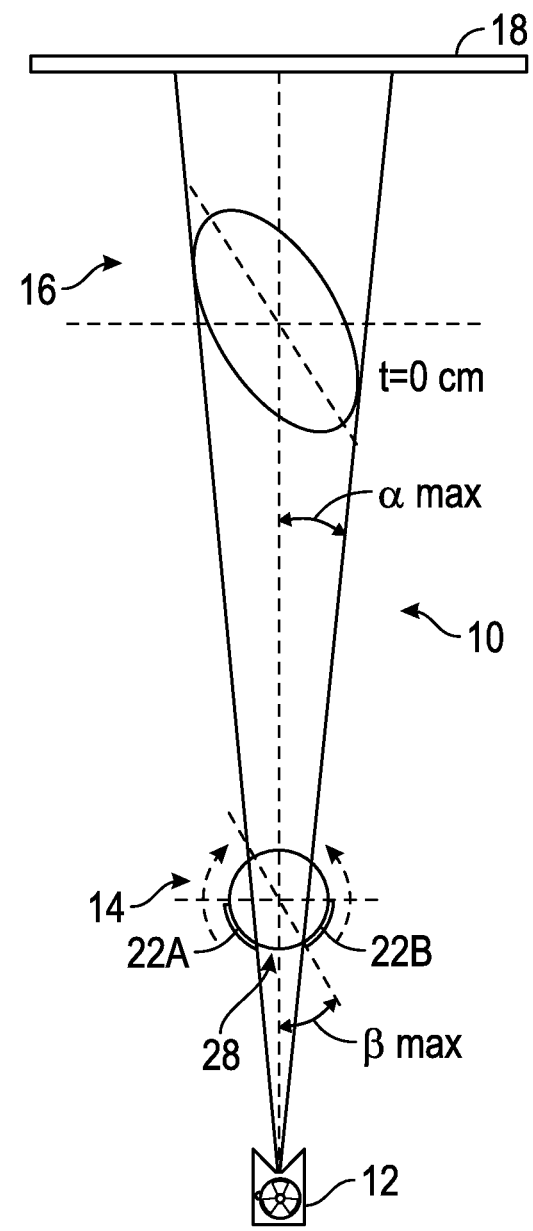
FIG. 1C  FIG. 1D

ADAPTIVE X-RAY FILTER USING SPATIAL EXPOSURE TIME MODULATION WITH DYNAMIC COLLIMATORS

CROSS-REFERENCE TO RELATED APPLICATIONS

This application is the U.S. National Stage of International Application No. PCT/US2016/045987, filed Aug. 8, 2016, which claims the benefit of U.S. Provisional Application No. 62/202,390, filed Aug. 7, 2015, which is incorporated by reference herein in its entirety.

FIELD

This disclosure relates to the field of radiographic imaging for medical applications, and more particularly to methods and devices for filtering and shaping a radiation beam based on a shape of a target object.

BACKGROUND

X-ray imaging is a consolidated technology that has reached high levels of excellence during more than a century of refinement. Conventional x-ray imaging systems include many individual components that function together to produce high quality radiographic images with the lowest possible radiation dose. Many x-ray imaging systems use a solid, stationary, beam-shaping filter—traditionally called a static bow-tie filter (see, e.g., FIG. 1A)—to differentially attenuate the central region and the periphery of the x-ray beam to compensate for the shape of the human body (or other object) cross-section, which is usually thicker in the center and thinner in the sides as seen from the x-ray source/focal spot. A traditional static bow-tie filter can serve several function, for example: reduction of the dose to the patient by avoiding unnecessary overexposure of the side of the body, reduction of the scatter coming from the overexposed areas, optimization of the detector dynamic range by avoiding saturation of the detector response in the periphery of the body, and generation of a uniform quantum noise level at substantially every pixel of the image (and correspondingly a uniform signal-to-noise-level).

The ideal shape of a static bow-tie filter is determined by the shape and material composition of the imaged object and the x-ray energy spectrum to be used. Imaging systems using a static bow-tie filter are therefore optimized to operate exclusively with a particular object size, shape, orientation, composition, and x-ray energy, and the performance of the system is reduced if the imaging parameters deviate from the ideal design parameters. To partially address this limitation, some clinical systems provide a small set of filters for the user to choose from, such as one filter for an adult person torso, one for head scans, or one for pediatric patients. However, these application-specific filters still fail to match the attenuation profile of most patients and do not provide optimal performance.

An imaging modality in which filters are of particular interest is computed tomography. In computed tomography, a filter can significantly reduce the radiation dose and mitigate some undesirable artifacts in the reconstructed images such as cupping. However, the practical performance of a static bow-tie filter is limited because the shape of the filter has to be designed assuming that the patient has a circular cross section and a fixed diameter. In this case, the same filter is used for most patients and for substantially every angle of rotation of the x-ray source around the patient. Since none of the human body parts have a circular cross section, the performance of the system is suboptimal. A technique known as automatic exposure control (or tube current modulation in tomographic imaging) can be used to scale the x-ray intensity used at each individual projection, and therefore compensate for the different maximum attenuation at different angles. However, this technique cannot correct for the different object profiles at different angles. The performance of a static bow-tie filter is further degraded in clinical practice for patients that are not perfectly centered on the axis of rotation of the scanner, which corresponds to the center of the symmetry of a static bow-tie filter.

SUMMARY

Disclosed herein are adaptive filters, radiographic systems, and methods for controlling the radiation exposure of a target object during a radiographic imaging procedure. An exemplary system comprises a radiation source, a radiation detector, and an adaptive filter positioned between the radiation source and the radiation detector. The system is configured to include a target object positioned between the adaptive filter and the radiation detector such that the target object can be radiologically imaged. The adaptive filter comprises first and second collimators (or just one collimator or more than two collimators) that block substantially all (or at least some) of the radiation that is incident upon the collimators, but allow radiation to pass between the collimators to reach the target object and radiation detector. The system is operable to move the first and second collimators apart from each other during a radiation emission from the radiation source such that the motion of the collimators allows different amounts of radiation from the radiation source to pass between the two collimators to each portion of the target object during the radiation emission.

Alternatively, the collimators can be moved from an open position to a closed position during the radiation exposure. The amounts of radiation allowed to reach each portion of the target object can be determined based on the thickness of each portion of the target object, as measured in the direction the radiation travels. The movement of the collimators can be such that the radiation detector receives a generally uniform distribution of radiation through a target object of varying thickness, such as for target objects that have a continuous reduction of thickness from the thickest part to the thinnest part (such as the path from the center to the periphery of a circle).

In some embodiments, the system is operable to move the first and second collimators apart from each other in opposite directions along curved paths about a common pivot axis. The common pivot axis can be generally perpendicular to the direction radiation travels. In other embodiments, the collimates move along linear paths toward and apart from each other.

In some embodiments, the adaptive filter includes a first motor to drive the first collimator and a second motor to drive the second collimator. For example, the collimators can be positioned between the two motors along the pivot axis.

In some embodiments, the system is operable to move the first and second collimators apart from each other from an initial closed position, wherein no radiation is allowed to reach the target object, to a plurality of increasingly further spaced apart positions that allow an increasingly greater portion of the target object to be exposed to the radiation. In some embodiments, the first and second collimators begin to move apart from each other near in time to when the radiation source begins to emit radiation toward the target object, and the first and second collimators reach a maximum separation from each other near in time to when the radiation source stops emitting radiation toward the target object. An opposite closing motion can alternatively be used, where the collimators start fully open and end closed together.

The collimators can move in a smooth, continuous motion or in a plurality of small steps such that the collimators stop briefly between each step. For example, the collimators can be moved about a pivot axis in 30 or more steps of less than 1° per step, and 1 millisecond or less can elapse between each step. Each step can be also subdivided in 8 or more smaller micro-steps, and 20 microseconds or less can elapse between each micro-step. The precise control of the collimators' rate of motion (determined by the changes in motor speed, or by the delay between consecutive motor steps), and the synchronization of the motion with the radiation exposure are fundamental components of certain systems and methods disclosed herein.

In some situations the effect that the adaptive filter has on the acquired x-ray projection image has to be corrected to recover a faithful radiography of the target object for clinical evaluation. Numerically combining the acquired image with the known spatial exposure time modulation profile produced by the adaptive filter allows the recovery of the radiographic image as it would look like without the filter. The correction process is similar to the standard flat field (or flood field) correction used with regular bow-tie filters. The spatial exposure time modulation profile of the adaptive filter can be experimentally measured by acquiring an image with the filter moving but no object inside the field of view, or it can be computationally estimated based on the pre-determined or measured collimator movement profile. Even in the non-ideal case in which the filter movement does not completely match the target object profile—due to mechanical limitations in the movement mechanism, or an irregular object shape—the corrected image will still keep some of positive features provided by the adaptive filter, such as a more uniform variance in the pixel values, fewer saturated pixels, and reduced object dose.

The foregoing and other objects, features, and advantages of the disclosed technology will become more apparent from the following detailed description, which proceeds with reference to the accompanying figures.

BRIEF DESCRIPTION OF THE DRAWINGS

FIG. 1A is a diagram illustrating the layout of radiological imaging system including a conventional static bowtie filter.

FIG. 1B is a diagram illustrating the layout of an exemplary radiological imaging system including a rotational adaptive filter.

FIG. 1C shows the imaging system of FIG. 1B with the adaptive filter in a closed position and FIG. 1D shows the imaging system of FIG. 1B with the adaptive filter in an open position.

DETAILED DESCRIPTION

Figure 1E:
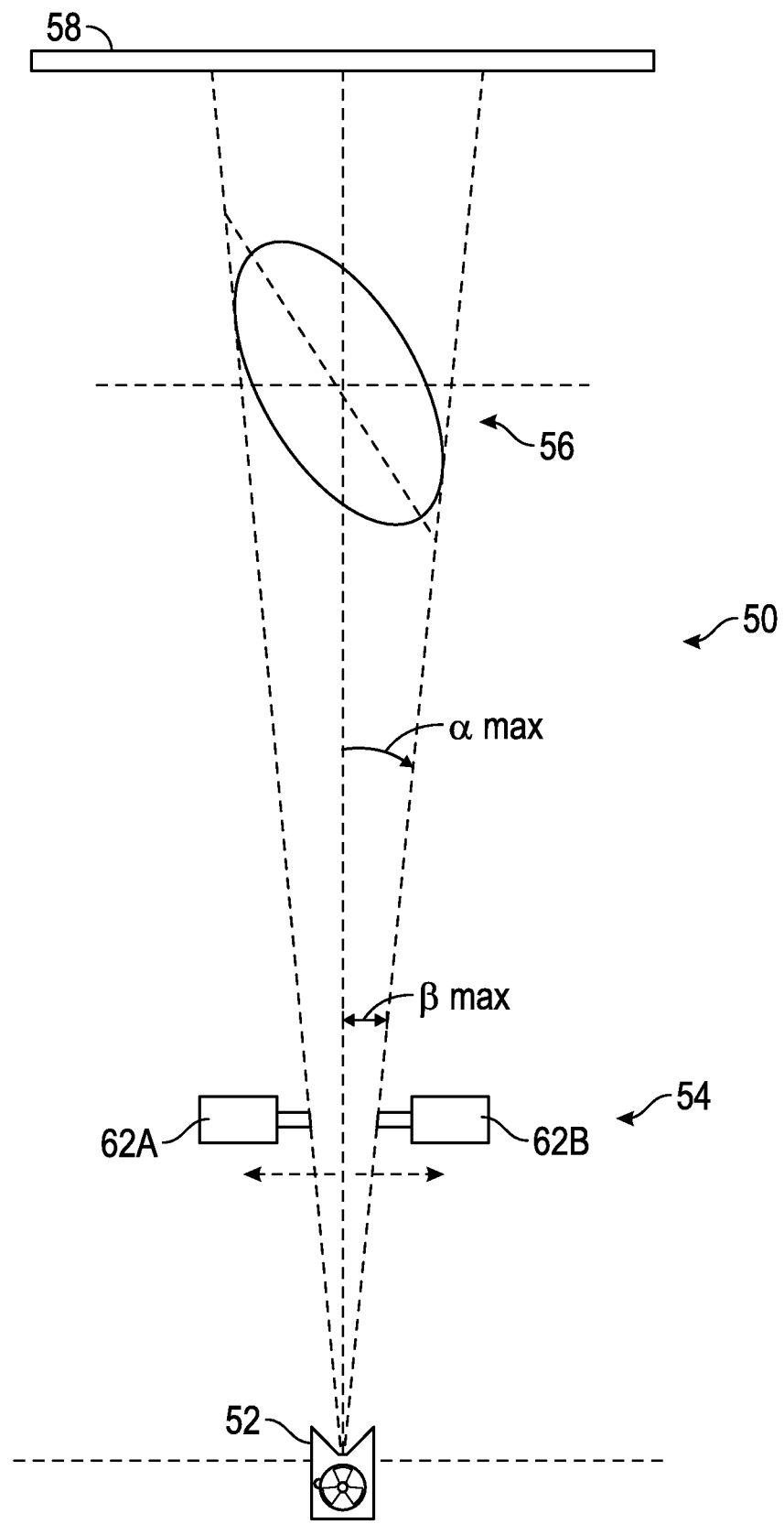
FIG. 1E is a diagram illustrating the layout of an exemplary radiological imaging system including a linear adaptive filter.

Disclosed herein are dynamic filters, and related systems and methods, that shape the radiation field using one or more completely (or partially) radio-opaque collimators that move during the image acquisition to modify the exposure time in different parts of the image. This concept is referred to herein as "spatial exposure time modulation." The concept is different from previous methods used to shape a radiation field that are based on a differential attenuation of the beam in different locations (with a substantially constant exposure time at every location). The disclosed dynamic filters that utilize spatial exposure time modulation are referred to herein as "adaptive bow-tie filters" or simply "adaptive filters." An adaptive filter provides many advantages of an ideal static bow-tie filter as well as the additional capability to adapt its motion in real-time during x-ray exposure to correspond to the profile of the imaged object (patient specific) instead of assuming a simple, fixed geometry for the object, like a traditional static bow-tie filter.

The described adaptive filters have conceptual similarities to a shutter in a photographic camera, but with a fundamental difference that the movable collimators in the adaptive filters can actively change the speed of the collimators during x-ray exposure following a pre-computed acceleration/motion profile to selectively block or attenuate the radiation emitted to different parts of the subject object, for example at the exact moment when the prescribed exposure has been reached. Contrary to a static bow-tie filter (see example static bow-tie system in FIG. 1A), the motions of the disclosed adaptive filters (see, e.g., FIGS. 1B-1E) can be synchronized with the start and/or the end of the x-ray exposure to provide the intended modulation. The synchronization can be implemented in an x-ray imaging system by coordinating the radiation source and the adaptive filter using a controller and/or control software. During the interval of time when the adaptive filter blocks all the field of view, the x-ray exposure to the object can be effectively null, or at least significantly reduced. Thus, an adaptive filter can also be used as an alternative method to implement automatic exposure control.

The disclosed adaptive filters and related systems and methods can be configured to reproduce profiles of many object shapes encountered in practical medical imaging applications. For example, a simple embodiment with a single movable collimator can reproduce the attenuation profile of an object with monotonically increasing attenuation, including angular views in a breast tomosynthesis system, without increasing the total exposure time (the total time can be determined by the most attenuating part of the object). The use of two collimators moving in opposite directions can reproduce the profile of an object with an attenuation profile increasing from the periphery to the center, such as an object with a circular or elliptical cross section. More complex attenuation profiles can be reproduced by adjusting the speed, attenuation, and shape of the collimators.

The adaptive filters can also be applicable for a fan-beam and for a cone-beam x-ray source. With a conical source, curved collimator edges may be used to modulate the beam. Additionally, a static bow-tie filter can be used concurrently with the disclosed adaptive filter to provide a baseline beam shaping. One or two collimators rotated 90 degrees with respect to the two initial collimators could also be used to modulate the radiation exposure in the perpendicular direction.

An example clinical implementation of the disclosed technology to improve the performance of computed tomography scanners includes a combination of software and hardware that compensates for the projection profile of an elliptical cylinder as seen from different rotation angles. The operator of the system (or an automatic system) can measure the principal axes of the ellipse that most closely resembles the shape of the part of the patient being scanned, and determine the location of the geometric center of the ellipse with respect to the center of rotation of the scanner. Using this information and other known parameters (such as the source-to-filter distance, the source-to-detector distance, the x-ray energy spectrum, an estimation of the average attenuation of the object, and the total exposure time) the software can compute the ideal dynamic filter movement sequence that would modulate the exposure time at each individual acquisition angle to compensate for the predicted shape of the ellipse as seen from the rotating source. A mathematical model of the attenuation profile for a target object having any shape can be used to compute an ideal adaptive filter movement profile at each source rotation angle (i.e., at each acquisition angle in a computed tomography scan). The profile of a non-cylindrical target object can change significantly at different angles, and therefore a fixed filter will not be able to adequately compensate for the object attenuation at more than one angle. An adaptive filter described herein can dynamically reproduce several different bow-tie filter profiles to provide improved system performance at every acquisition angle.

FIGS. 1B-1D show plan view diagrams illustrating an exemplary radiological imaging system 10 including an exemplary rotational adaptive filter 14 positioned between a radiation source 12 and a test object 16, with a radiation detector 18 positioned behind the test object. FIG. 2 shows an exemplary clinical embodiment of the imaging system 10 configured for breast imaging.

Figure 2:
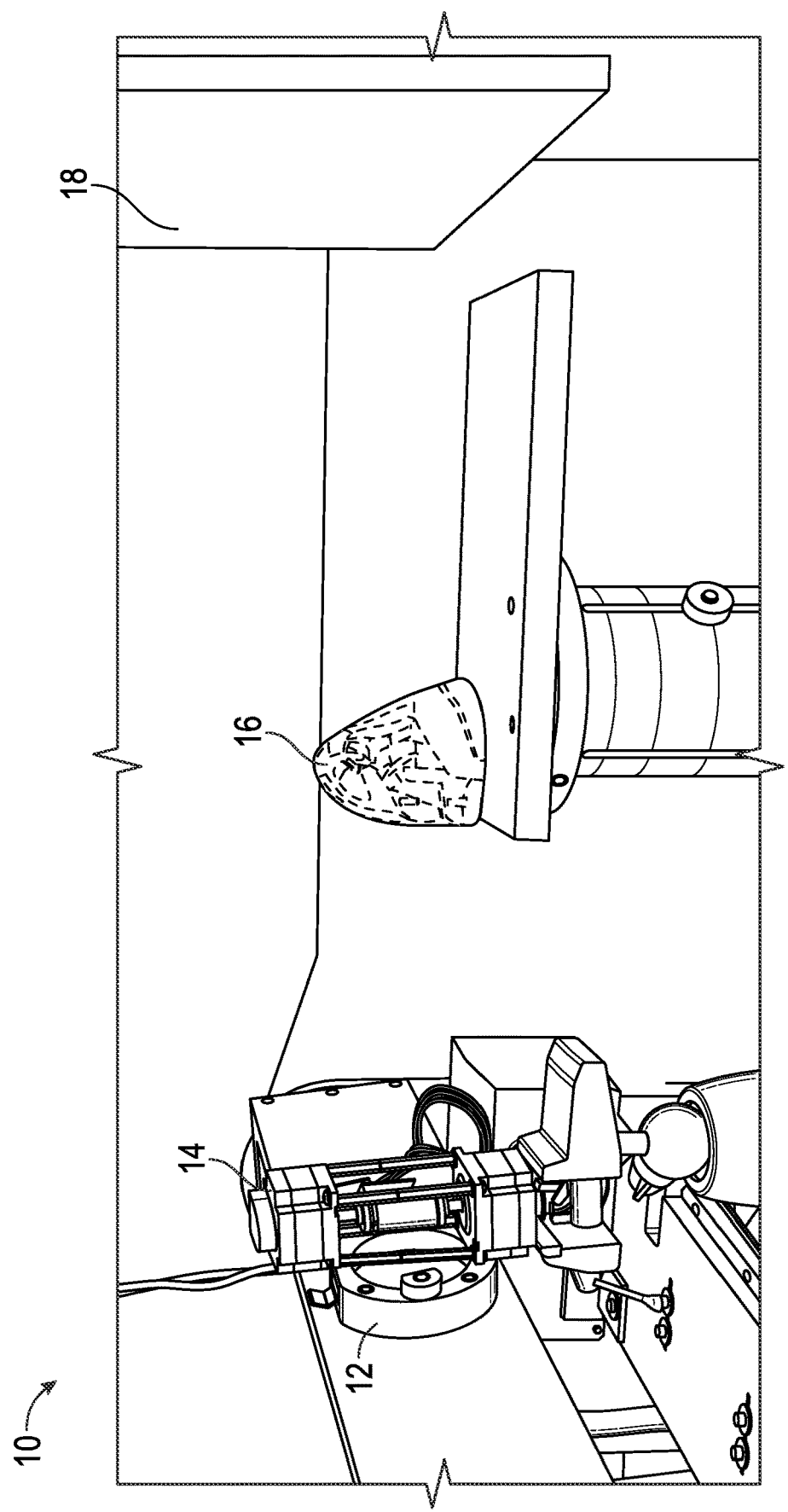
FIG. 2 shows an embodiment of the imaging system of FIG. 1.

FIG. 1E is a plan view diagram illustrating another exemplary radiological imaging system 50 that includes an exemplary linear adaptive filter 54 positioned between a radiation source 52 and a test object 56, with a radiation detector 58 positioned behind the test object. Instead of the collimators of the adaptive filter moving in rotational motion, as in the system 10, in the system 50 the collimators of the adaptive filter 54 move toward and apart from each other in linear motions, such as in a common plane. They can be driven by linear actuators 62A, 62B, such a voice coil actuators, for example, rather than a rotational motor.

Figure 3B:
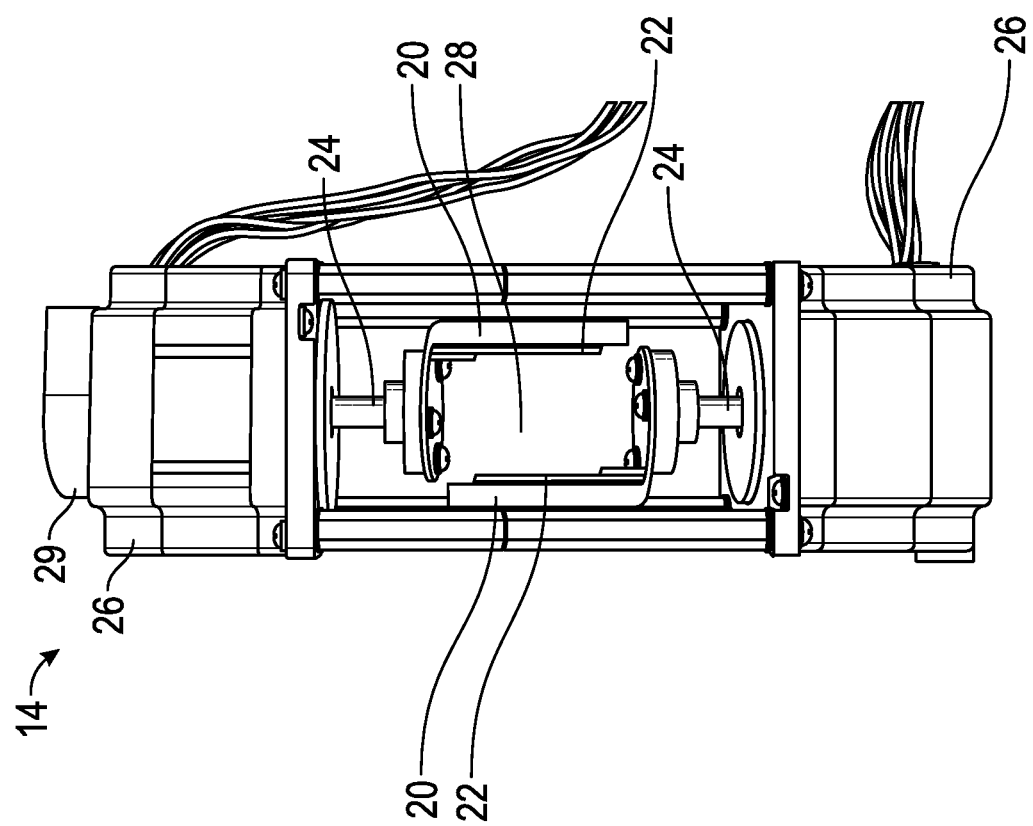
FIGS. 3A and 3B show the adaptive filter of the system of FIG. 2 in closed and open positions.
Figure 3A:
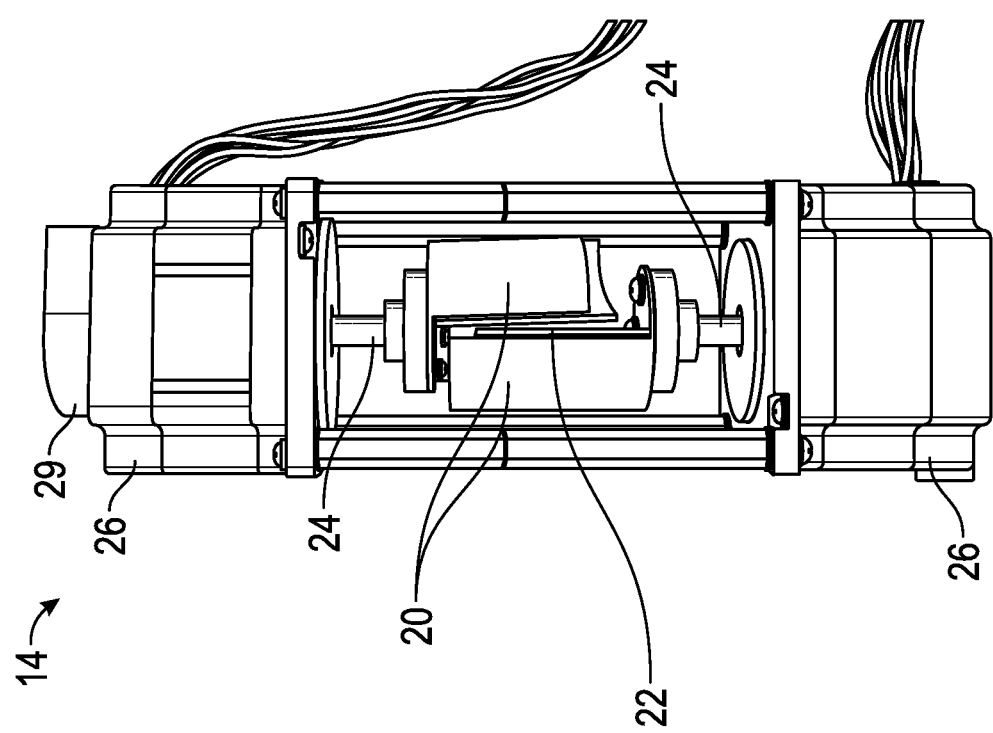
Figure 4:
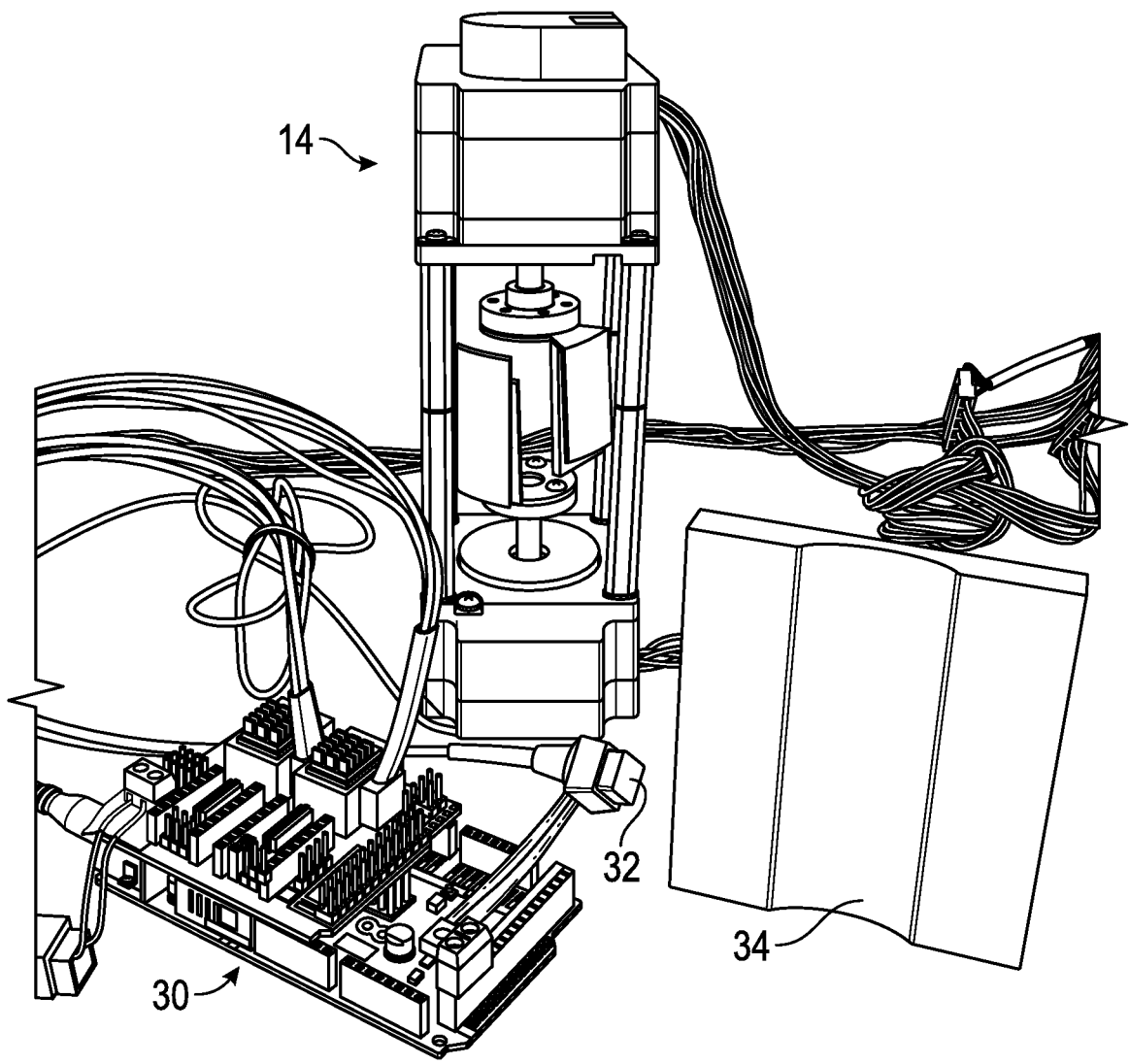
FIG. 4 shows the adaptive filter of FIGS. 3A and 3B along with control components. A conventional static bow-tie filter is also illustrated for comparison.
Figure 5A:
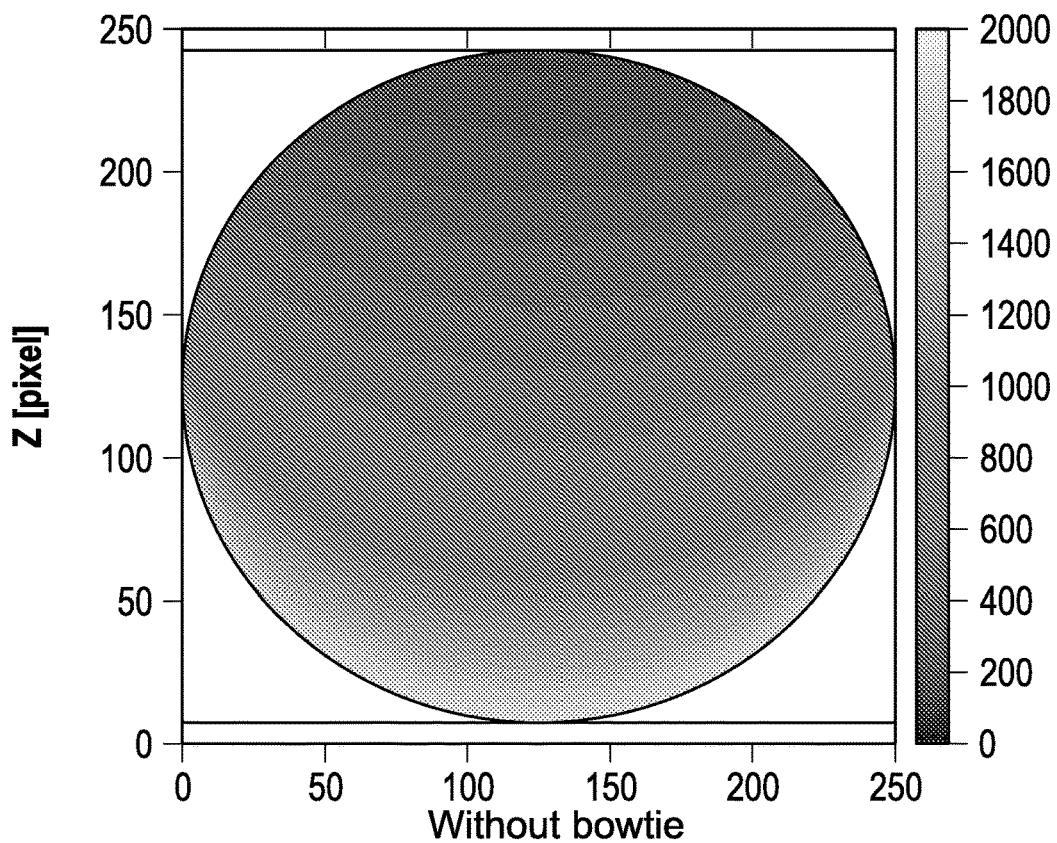
FIGS. 5A-5D are simulation results showing 2D dose distribution in a cylindrical object with a 5 cm radius for a single x-ray projection at 0 degrees without a filter (5A) and with an adaptive filter (5B); and graphs showing corresponding average and peak dose values for a single projection (5C) and the cumulative dose for 360 projections acquired around the object (5D).
Figure 5B:
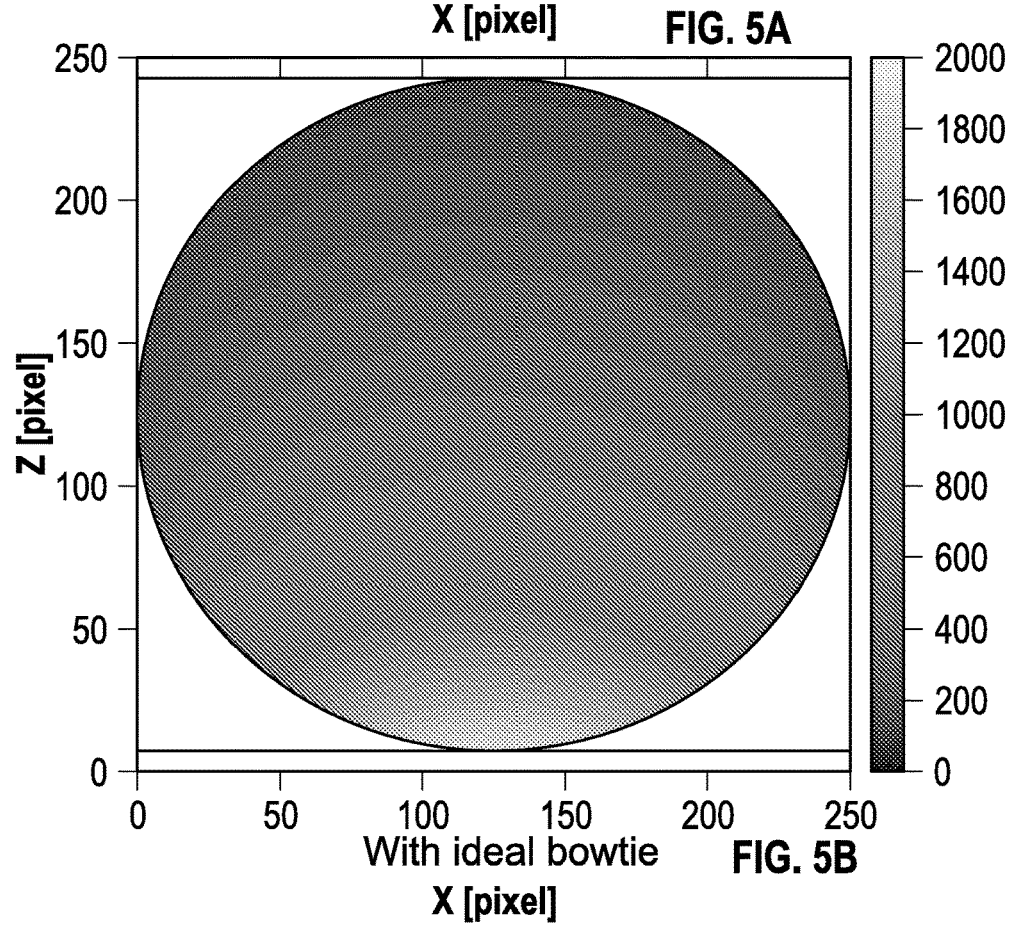
Figure 5C:
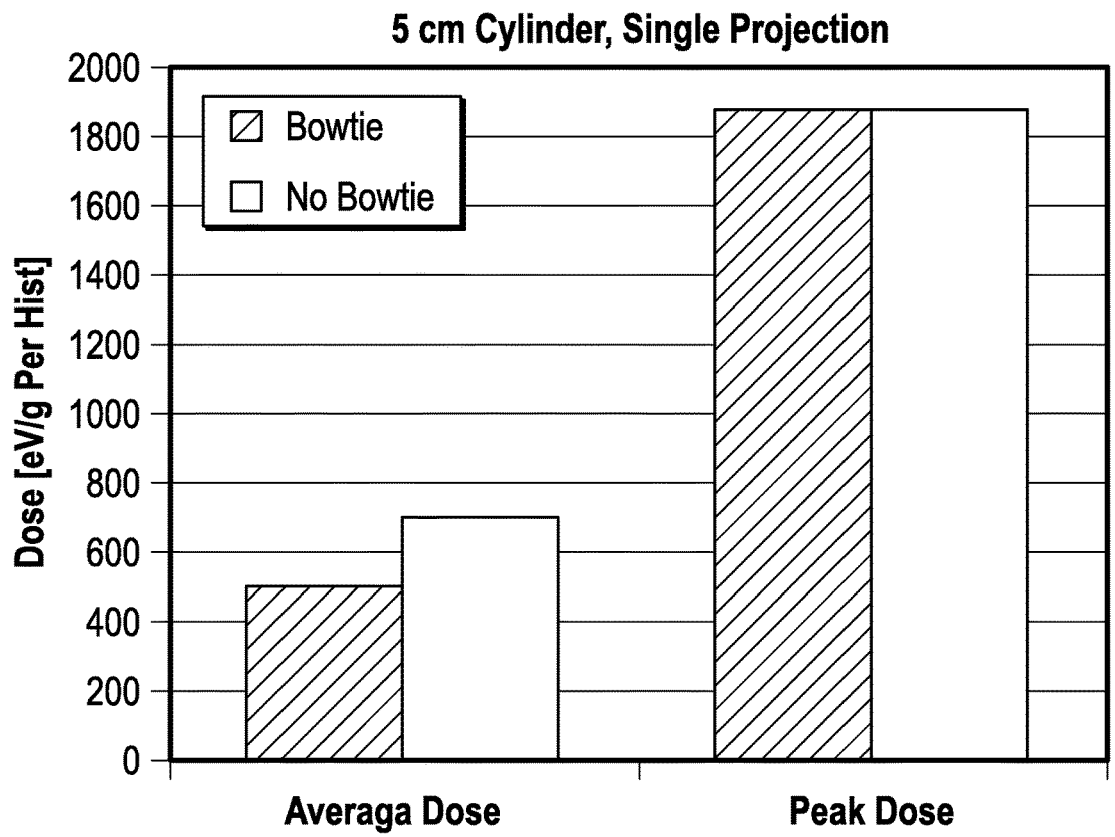
Figure 5D:
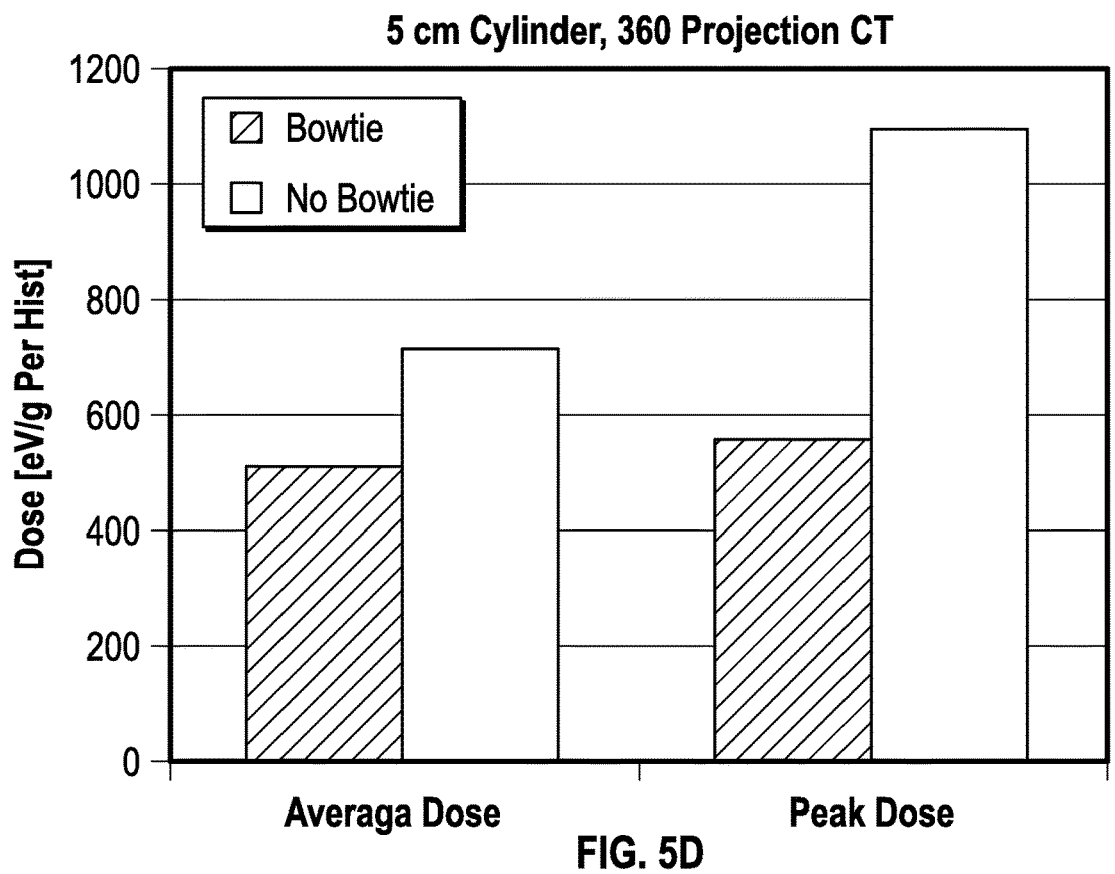

FIGS. 3A, 3B, and 4 illustrate an exemplary rotational adaptive filter 14 that comprises two stepper motors 26 rotating in opposite directions and two collimators or shields 22 (or other radio-opaque shields) coupled to coaxial motor shafts 24 via retainers 20. In other embodiments, a single motor can control both collimators. In some embodiments, the collimators 22 can block substantially all of the radiation that is incident upon them, as opposed to attenuating the radiation so that a portion of radiation gets through. In other embodiments, the collimators can block a portion of the radiation incident upon them and allow a portion to pass through them. In such embodiments, the algorithm used to compute the motion profile of the collimators can take into account the amount of radiation that travels through the collimators in order to produce the desired beam shaping. Constructing the collimators with an appropriate combination of materials (such as aluminum, copper, carbon, polymers, and/or other materials), the energy spectrum of the radiation traveling through the collimators can be customized to reproduce the energy spectrum of the radiation traveling through a certain radiographic thickness of the patient tissue in a way that minimizes the beam hardening effect artifact (e.g., producing a substantially uniform energy spectrum at substantially every pixel of the detector, both at the center and at the periphery of the object). The motors 26 can rotate the two collimators 22 in opposite directions in order to open or close the field of view window 28 of the object 16 as seen from the radiation source 12. Two separate motor controllers can be used to independently regulate the speed of rotation of each collimator 22. If the device is constructed with stepper motors, the speed of the stepper motors 26 can be effectively modulated by modifying the time period between consecutive micro-step pulses, producing an effectively smooth rotation movement with continuously varying speed. If the device is constructed with motion mechanisms other than stepper motors (such as regular electric motors with or without gears, linear actuators, magnetic solenoids, or shape-memory alloys) alternative electronic speed control methods can be employed. The adaptive filter 14 is located near the exit window of the radiation source 12, and before the object 16 (pre-patient collimation).

FIG. 3A shows the adaptive filter 14 with the rotatable collimators 22 completely closed and FIG. 3B shows the adaptive filter with the rotating collimators open to provide a window 28. During the x-ray image acquisition, the accurately timed movement of the edges of the collimators 22 limits the beam width starting from the center of the object 16 towards the periphery to compensate for the known object profile. The radio-opaque collimators 22 can comprise, for example, lead panels. The collimators can have any thickness sufficient for the amount of radiation present, such as a thickness of 2 mm or more, to provide complete or partial x-ray attenuation as desired. The collimators 22 can be mounted in and/or coupled to structural retainers 20 as illustrated. This thickness of collimators can be sufficient to fully attenuate the x-ray beam quality used in an example breast imaging procedure. The retainers 20 can comprise any material, such as a 3-D printed or molded polymeric material, and can couple the collimators 22 to the motor shafts 24. The collimators 22 can also be directly coupled to the motor shafts 24 in some embodiments. The collimators 22 can have straight, parallel opposing edges, as shown, or can have other non-straight edge profiles.

The motors 26 can be configured to move the collimators 22 in a step-by-step motion, or in a continuous analog motion. The motors 26 can comprise stepper motors that can move the collimators 22 any rotational distance per step, such as less than 2.0° per step, less than 1.0° per step, and/or from about 0.8° to about 0.9° per step. The motor drivers can be set to divide each full motor step into a plurality of smaller steps, such as 32 micro-steps, for high resolution motion. In some embodiments, the motors can comprise or be coupled to a gearing system that reduces the motor's rotational motion to slower, more precise motions for the collimators. In embodiments with linear actuators driving the collimators toward and apart in linear paths, such as the system 50, the collimators can analogously be moved in incremental linear steps.

In some embodiments, the motors, the collimators, the retainers, and/or other system components can include position encoders for implementation of a closed-loop feedback and control system to measure and validate the collimator edge position (e.g., the collimator edge rotation position and angle in a rotational embodiment, or linear position in a linear embodiments). For example, the rotational device 14 shown in FIGS. 3A and 3B can include a position encoder 29. In some embodiments, the shaft of each motor can extend above/below the motor enclosure to allow the optical encoder 29 to accurately measure its rotation. The encoder 29 can be electrically coupled to a control system 30 (see FIG. 4). In some embodiments, end-stop switches (e.g., optical end-stop switches) can be added to the system to reliably position the collimators at a known angle (for example, to position the collimators in a closed position corresponding to angle 0), and to prevent an accidental collision between the collimators (depending on the construction of the device such a collision might or might not be physically possible). In some embodiments, the system can comprise a voice coil actuator that uses an analogic resistor as a position encoder (not optical), which can provide absolute position information at 10 micron resolution for example.

Figure 3C:
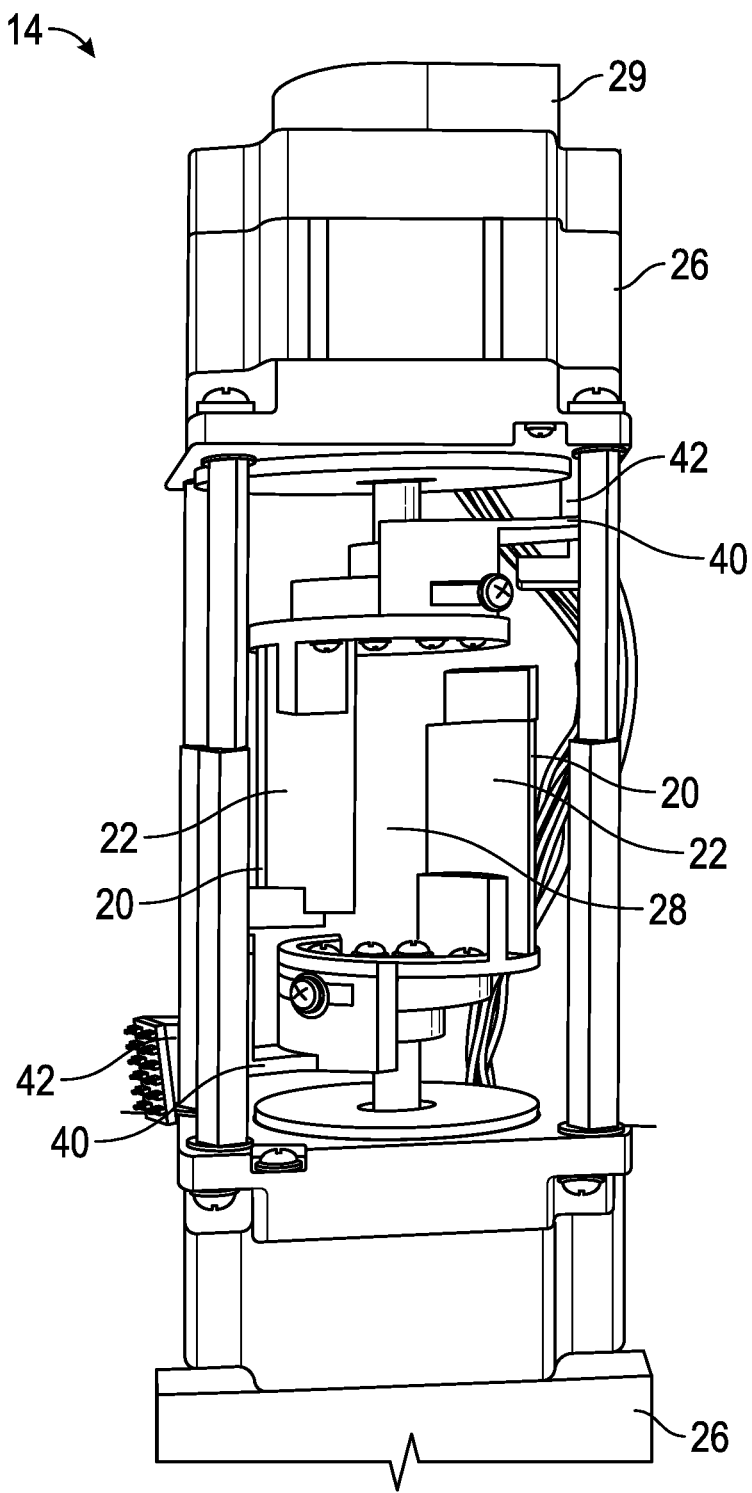
FIG. 3C shows another exemplary adaptive filter including optical end-stops that enable a more accurate and reliable positioning at high speeds.

FIG. 3C shows a variation of the rotational adaptive filter 14 that includes optical end-stops 40 coupled to the retainers 20 and stationary optical sensors 42 that sense the position of the end-stops 40 to enable a more accurate and reliable positioning of the collimators 22 at high speeds. Coupled with one or more optical encoders, the end-stops and sensors can be used to optically detect the exact position of each collimator in real time and feed the position data back to the controller for more precise control of the collimators. Sensors or encoders that directly measure the real motion profile of the collimators provide information that can be used to validate that the device has moved according to the pre-computed profile, and/or to estimate the degree of deviation between the pre-computed and real profiles. Accurate knowledge of the real device motion, and the corresponding beam shaping, can be important in applications where the radiographic images have to be normalized by a flat field image (e.g., an image of the filter doing the same motion profile but without the object).

As shown in FIG. 4, the disclosed systems can also include a control system 30 that includes a microcontroller and stepper motor drivers that are electrically and/or optically coupled to the motors of the adaptive filter. The microcontroller can, for example, calculate and execute a step-by-step movement sequence of the collimators (a movement profile) sufficient to compensate for a particular object shape. The object parameters can be pre-programmed or input by a user, or can be sensed or determined prior to radiological imaging using an optical or non-optical detection system, or using an initial x-ray scout radiograph of the patient, for example.

In some systems, the object's profile is determined by an optical system that includes one or more optical cameras, and the determined profile is communicated to the control system 30 for the adaptive filter to determine the movement profile that the collimators will move through during a radiation exposure (whether rotational or linear or otherwise).

The system can optionally include a manual movement trigger button 32 (FIG. 4). In other embodiments, the system can comprise automatic triggering, and control of the adaptive filter can be achieved by coupling the control system 30 to the radiation source trigger output. Alternatively, an electronic radiation sensor, such as a diode or phototransistor connected to the filter's microcontroller, could be used to independently detect the start of the x-ray irradiation and trigger the collimator movement. For example, the collimator movement can begin automatically when incoming radiation is detected.

FIG. 4 also shows an example of a conventional static bow-tie filter 34 (e.g., made of aluminum) for comparison. Such a static filter is suitable only for a specific object size, distance, orientation, and energy spectrum. The partial attenuation of the beam with a static bow-tie filter can also produce unwanted scatter contamination that is avoided with the disclosed adaptive filter, which can provide a binary 100% or 0% transmission technology.

FIG. 1B is a plan view diagram illustrating the system 10 with relevant dimensions and angles labeled. In this view, the adaptive filter 14 is shown in horizontal cross-section with the two collimators 22A, 22B being movable along a circumferential path having a radius Rb. Each collimator 22A, 22B has a curved profile matching the curvature of the circumferential path, and an arc length between 0° and 90°. In some embodiments, the arc length of each collimator is from 0° to 60°, from 0° to 45°, from 0° to 30°, from 30° to 60°, about 45°, and/or other arc lengths. The two collimators can have the same arc length or different arc lengths.

As the two collimators 22A, 22B move apart from each other, the angle $\beta$ for one or both of the collimators increases from 0°. At the same time, the aperture window 28 opens and the angle $\alpha$ increases corresponding to an increasingly wider and wider sector of radiation that is allowed to pass through the adaptive filter 14 to the object 16. The relationship between the angles α and β is dependent on at least the radius Rb of the adaptive filter and the distance sbd between the radiation source 12 and the center axis of the adaptive filter 14. During a radiation exposure, the collimators 22A, 22B can move with a velocity and acceleration that is predetermined based on the cross-sectional shape profile of the object 16, as well as the object's position relative to the source 12 and filter 14. The angles α and β can also depend on the distance sod from the source to the object 16 and/or the distance sdd from the source to the detector 18.

FIG. 1C shows the system with the collimators 22A, 22B closed, such that α=0 and β=0 and no radiation passes through the filter 14. FIG. 1D shows the system with the collimators 22A, 22B rotating apart in opposite circumferential directions so that radiation passes through the aperture window 28. In FIG. 1D, the right collimator 22B is at an angle β and the left collimator 22A is at a similar angle, though the two collimators can be at asymmetric positions depending on the shape of the object 16.

In some methods, during a single radiation exposure, the collimators 22A, 22B can move from a closed position (FIG. 1C) at the beginning of the radiation exposure to a maximum open position (e.g., FIG. 1D) at the end of the radiation exposure. In other methods, the collimators 22A, 22B can move from a starting open position (e.g., FIG. 1D) at the beginning of the radiation exposure to a closed position at the end of the radiation exposure. In other methods, the collimators 22A, 22B can move from a closed position at the beginning of the radiation exposure to a maximum open position and then back to a closed position at the end of the radiation exposure. For example, the final closed position can be the same as the starting closed position (including a change of direction at the maximum open position), or the final closed position can be with the collimators on the opposite side of the circumferential path from where they started (e.g., they can start closer to the radiation source and end closer to the object). Similarly, in other methods, the collimators can start open, move to or toward a closed position and then move back to an open position at the end of the radiation exposure. If multiple images are acquired sequentially in a short amount of time, for example during a computed tomography scan, the images can be acquired with alternating opening and closing motions of the collimators to avoid repositioning the collimators between exposures.

For some objects such as objects with an elliptic cross-section, an accurate beam shaping is more relevant near the edges (where the curvature is large) than in the center (where the curvature is low, and the object thickness is nearly constant). In this situation, the collimators can be moved only for a short distance near the periphery of the object, shaping the beam only in the edge of the object where it is most relevant. With less travel distance for the same exposure time, the peak speed of the collimators can be reduced. More complex movement profiles during an exposure are also achievable with the disclosed technology.

In addition, the two collimators 22A and 22B can move independently of each other and in asymmetric movement profiles. The motion of each collimator can depend on the shape of the portion of the object 16 that is behind each collimator. If the object has a symmetric profile, such as a circle or an ellipse that has its major or minor axis aligned with the longitudinal axis of the system (the axis passing through the source point 12 and the rotation center axis of the adaptive filter 14), then the two collimators 22A, 22B may move with motions that are symmetric about the longitudinal axis. However, if the object is not symmetric about the longitudinal axis (such as the object 16 shown in FIG. 1B, or if the object is shifted laterally out of line with the longitudinal axis), then the two collimators can have asymmetric motions with different speed profiles to provide a desirably even radiation dose across the asymmetric object. In addition, with an asymmetric object, the maximum opening angle β max can be different for each collimator. In an extreme example, if the object 16 is located entirely on one side (e.g., to the right side) of the longitudinal axis of the system, one of the collimators (e.g., the left collimator) may not move at all while the other collimator moves during the exposure. For objects that are not aligned with the imaging system central axis, the closed position of the filter can be modified by rotating both motors a certain amount of degrees in the same direction to make sure that the most attenuating part of the object is always irradiated for the longest time. Due to these independent motions available for each of the collimators, and the precisely controllable speed and timing of the collimator motion, the disclosed system can be used for x-ray imaging of a wide variety of object shapes, whether they are aligned or misaligned with the longitudinal axis, and can do so while providing a more even radiation dose across the whole object and/or a more even radiation level received at the x-ray detector 18 behind the object 16.

The presence of the adaptive filter 14 in the imaging system 10 modifies the appearance of the x-ray image acquired by the detector 18. The effect of the filter can be corrected to recover a faithful radiography of the target object that can be used for evaluation of the internal object geometry. A possible method to perform this correction would be similar to the standard flat field correction used with regular bow-tie filters. In this process, the acquired image is combined with the known spatial exposure time modulation profile produced by the adaptive filter to recover the image that would have been produced if the filter had not spatially modified the exposure time. The spatial exposure time modulation profile of the adaptive filter can be experimentally measured by acquiring an image with the filter moving without any object inside the field of view (an image typically called a flat field or a flood field). The profile can also be computationally estimated based on the pre-determined collimator movement profile, or based on the actual movement profiled measured during the image acquisition.

The collimators 22A, 22B can have various shapes. They can be curved about a center rotation axis as shown, or can have other curvatures, such as three-dimensional curvatures (e.g., spherical curvature), or can be flat plates without any curvature. The collimators 22A, 22B can have straight, vertical edges as shown, or can have straight, non-vertical edges or non-straight, curved edges. The edges may or may not be parallel. For example, for a cone-shaped radiation beam, the collimators can have curved adjoining edges that form a circle, ellipse, or other joint shape from the view point of the radiation source.

In some embodiments, the collimators 22A, 22B can move linearly rather than in a circular motion (as in the system 50 shown in FIG. 1E). In some embodiments, the collimators can move in a curved but non-circular motion. In some embodiments, the collimators can move in three dimensions. Regardless of the motion path, whether curved or linear, the principles and methods disclosed herein can be equally, or at least analogously, applied.

In some embodiments, two rotational collimators can start on opposite sides of the circumferential path illustrated in FIG. 1B and can move in the same circumferential direction during the exposure. For example, the collimator 22A can start at the position shown in FIG. 1C while the other collimator 22B can start at a position at the rear of the circumferential path that is diametrically opposite from the position of the collimator 22A. As the collimator 22A moves clockwise rearwardly around the left side of the path, the collimator 22B can move clockwise forwardly around the right side of the path.

In some embodiments, only one collimator is present, and the single collimator can have at least one position where it fully blocks the view of the object from the radiation source, and can move to another position where it fully exposes the object from the view point of the radiation source. In other embodiments, the adaptive filter can comprise three or more collimators. For example, two pairs of collimators moving at the same time along two perpendicular directions could be used to modulate the beam shape in two dimensions (e.g., in the vertical and horizontal directions).

In some embodiments, both of the collimators 22A, 22B are driven by motors located on the same end of the rotation axis, such as both of the motors 26 being above the collimators or both of the motors being below the collimators. In such embodiments, the two motor shafts 24 can be concentrically position with one within the other. In some embodiments, a single motor 26 and/or a single motor shaft 24 can drive both of the collimators 22A, 22B. In other embodiments, linear movement actuators can move the collimators within a plane (as in FIG. 1E).

An exemplary adaptive filter technique was evaluated using computer simulations. A Monte Carlo simulation code MC-GPU was used to estimate the radiation dose distribution inside two test objects, with and without the adaptive filter. A typical case representative of a breast computed tomography acquisition was simulated. The mathematical function used to model the adaptive filter spatial exposure time modulation profile in the simulations is the same implemented in the prototype adaptive filter microcontroller's firmware to guide the collimator motion profile.

The simulation results presented in FIGS. 5-7 show that the use of an ideal filter that closely matches the imaged object shape and size can produce a reduction of the average dose received by the object between 28% and 68% for a single projection image, and between 28% and 55% for a complete tomographic acquisition. The peak dose in the tomography is reduced more than 50% due to a more uniform distribution of the x-ray flux. The disclosed dynamic filtering scheme proved to work equally well with a cylindrical object and an elliptical object, contrary to a static filter that is not able to compensate for an asymmetric shape. This limitation of static filters is visualized in FIG. 1A by the fact that the angle alpha is fixed (e.g., equal in both sides), and the fan beam aperture is substantially larger than the object.

FIGS. 5A-5D are simulation results showing 2D dose distribution in a cylindrical object with a 5 cm radius for a single x-ray projection at 0 degrees with the adaptive filter (5B) and with no filter (5A); and graphs showing corresponding average and peak dose values in a single projection (5C) and the cumulative dose deposited in the object by 360 projections acquired around the object in one degree increments reproducing a computed tomography scan.

Figure 6A:
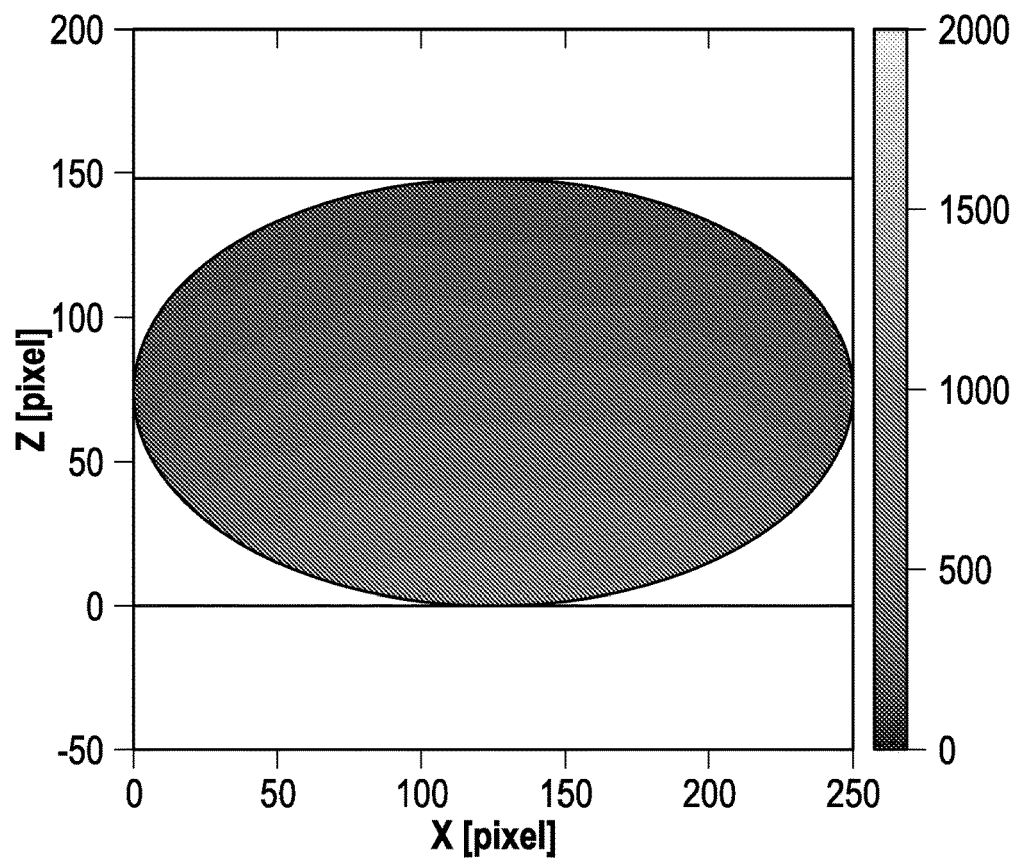
FIGS. 6A-6C are simulation results showing 2D dose distribution in an elliptical object (5 cm and 3 cm radii) for a single x-ray projection at 0 degrees with adaptive filter (6A) and no filter (6B); and a graph showing corresponding average and peak dose values (6C).
Figure 6B:
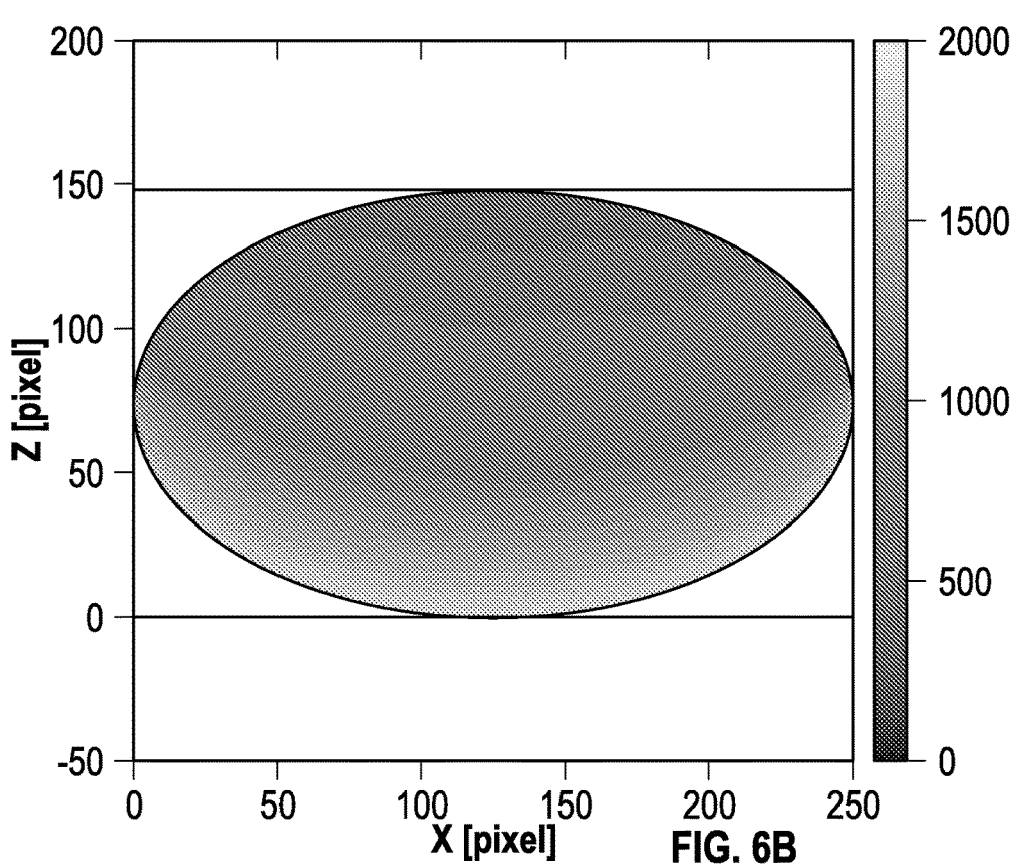
Figure 6C:
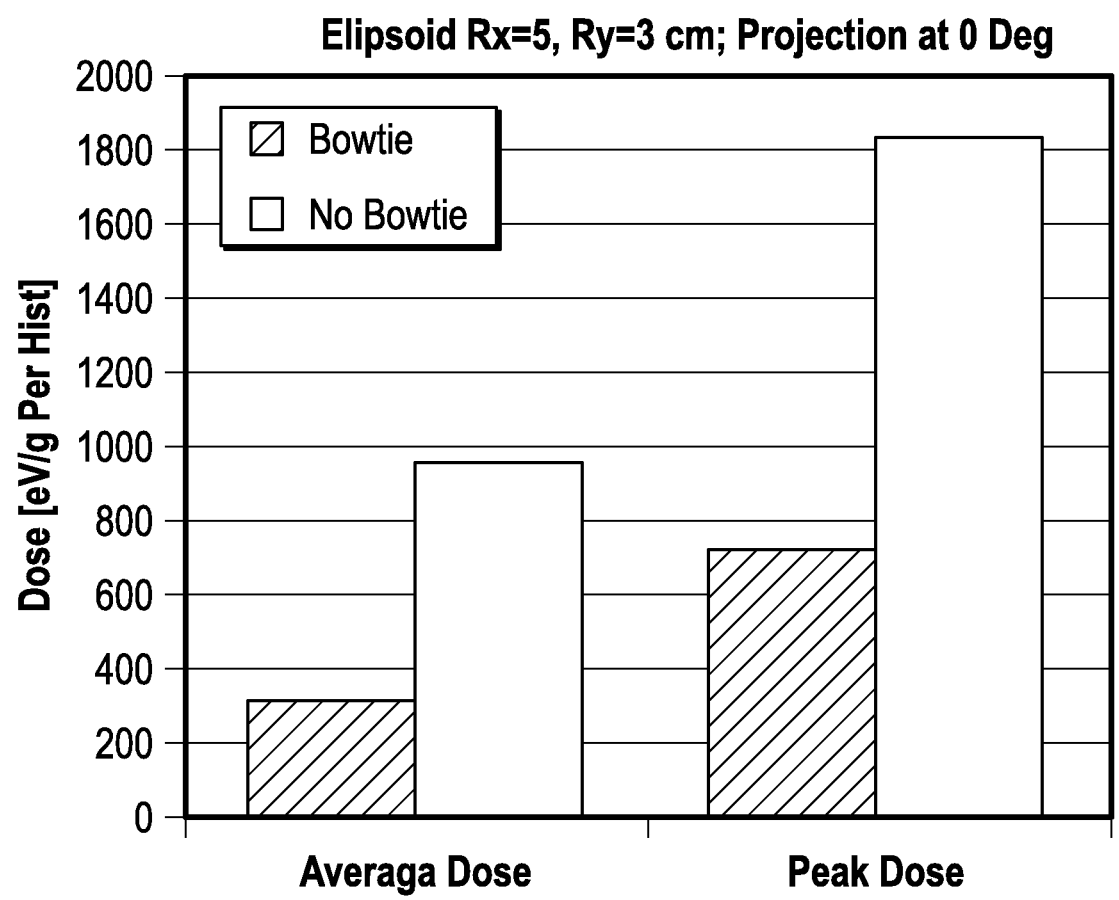

FIGS. 6A-6C are simulation results showing 2D dose distribution in an elliptical object (5 cm and 3 cm radii) for a single x-ray projection at 0 degrees with the adaptive filter (6A) and with no filter (6B); and a graph showing corresponding average and peak dose values (6C).

Figure 7A:
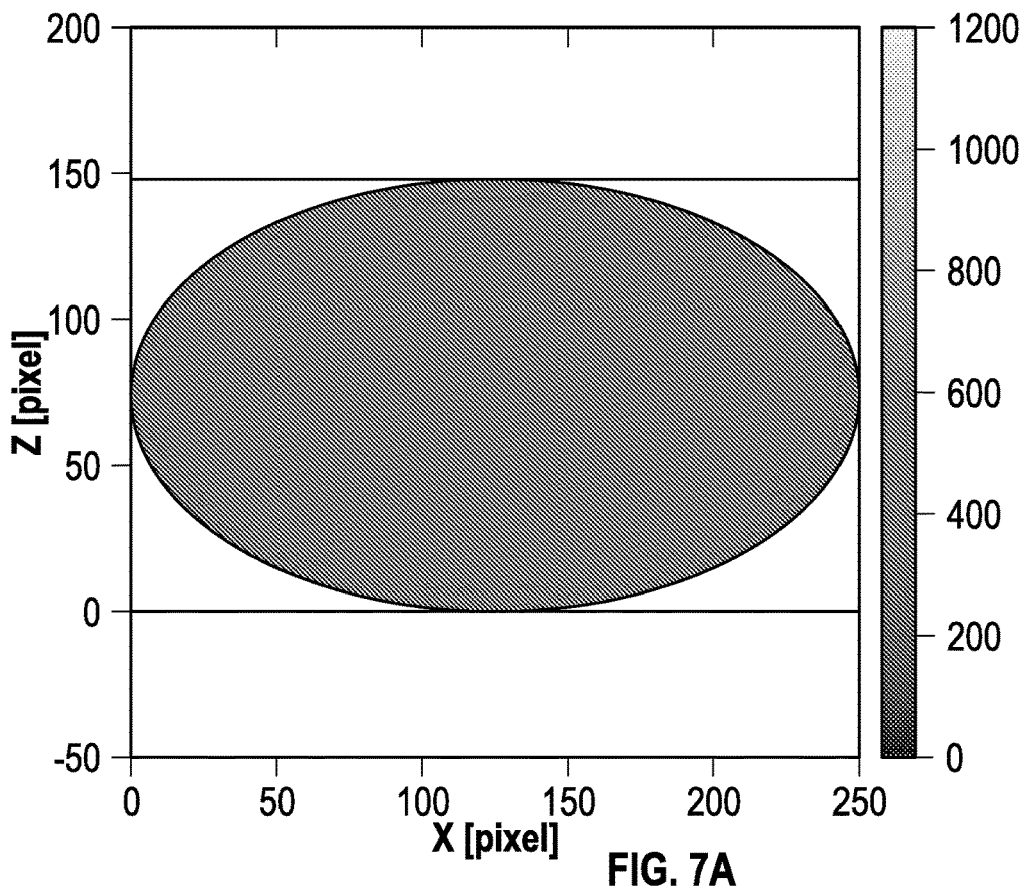
FIGS. 7A-7C are simulation results showing 2D dose distribution in an elliptical object (5 cm and 3 cm radii) for 360 tomographic projections around the object (source-to-rotation axis distance 50 cm) with an adaptive filter (7A) and with no filter (7B); and a graph showing corresponding average and peak dose values (7C).
Figure 7B:
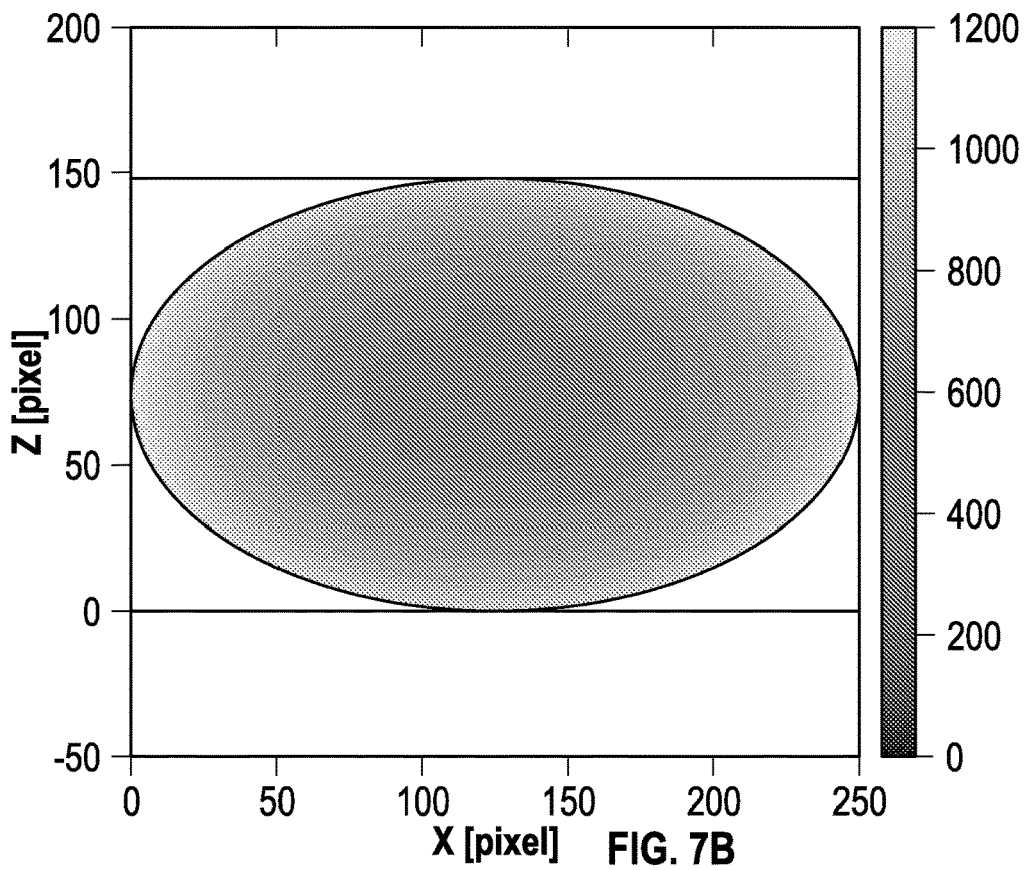
Figure 7C:
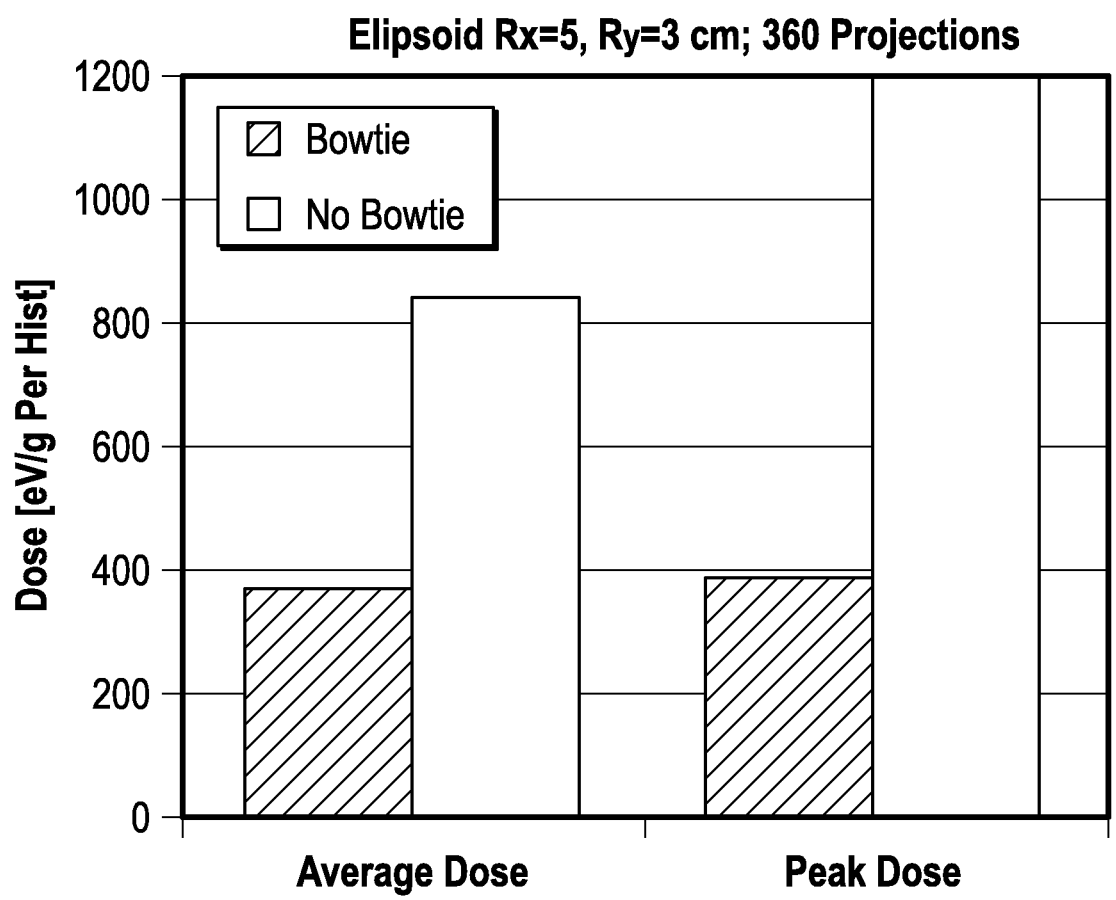

FIGS. 7A-7C are simulation results showing 2D dose distribution in an elliptical object (5 cm and 3 cm radii) for 360 tomographic projections around the object (source-to-rotation axis distance 50 cm) with the adaptive filter (7A) and with no filter (7B); and a graph showing corresponding average and peak dose values (7C).

Figure 8:
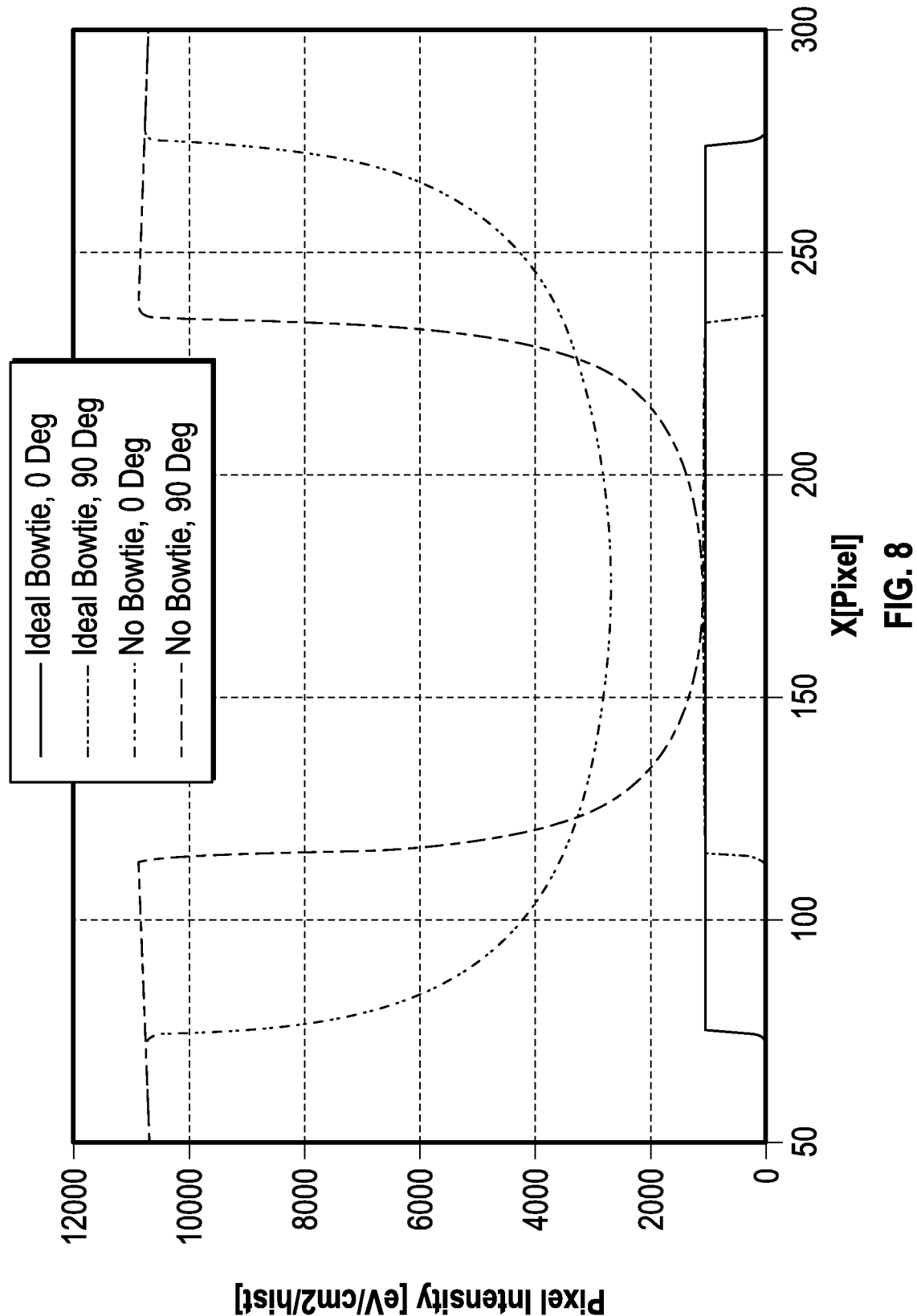
FIG. 8 is a graph illustrating theoretical x-ray profiles detected by a 1D detector behind an elliptical object, with and without an ideal adaptive filter.

FIG. 8 shows theoretical x-ray profiles detected by a one dimensional detector behind an elliptical object, with and without the adaptive filter, at 0° and 90° acquisitions. Embodiments of the disclosed adaptive filters can produce a uniform profile at any acquisition angle. The uniform intensity of the image with an adaptive filter can match the lowest intensity obtained without the adaptive filter at the maximum attenuation projection (90°), for example. In clinical practice, the irradiation parameters may be set to produce a valid image at the maximum attenuation projection, and all other less-attenuating projections can receive more radiation than the minimum required. Overexposure can translate into a noise level unnecessarily below the minimum noise acceptable for the task at the cost of increased dose to the patient. With the disclosed adaptive filters, substantially all of the projections can have about the same noise level and the dose is minimized. An additional feature of some adaptive filters is that they can block substantially all, or most, radiation outside the lateral edges of the object, where the signal intensity would be largest without the adaptive filter. Stopping the unnecessary radiation outside the sides of the patient prevents undesired effects on the detector that can reduce the system performance such as detector saturation, optical glare contamination, and backscatter.

The adaptive filter of FIG. 3C was tested in a bench-top x-ray imaging system in two different validation experiments. In both, an x-ray source with a tungsten anode operated at 45 kVp, 32 mA, and 500 ms exposure time was used. The source-to-adaptive filter distance was 14 cm, and the source-to-detector distance 100 cm. During each x-ray exposure the adaptive filter opened in 160 ms following the computed movement profile from a closed position up to the expected edge of the object, and then closed in 160 ms more, producing an effective exposure time of 320 ms at the center of the object (and a lower exposure time at the periphery). The opening and closing movements were each divided in 2000 micro-step movements, approximately.

Figure 9C:
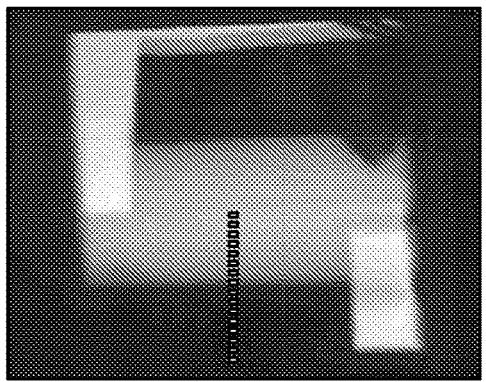
FIGS. 9A-9F shows flood-field projections of an exemplary adaptive filter in a an open position (9A) and moving during an exposure (9B-9F) to compensate for five different sized cylindrical objects (radii of 2 cm, 3 cm, 4 cm, 5 cm, and 6 cm).
Figure 9F:
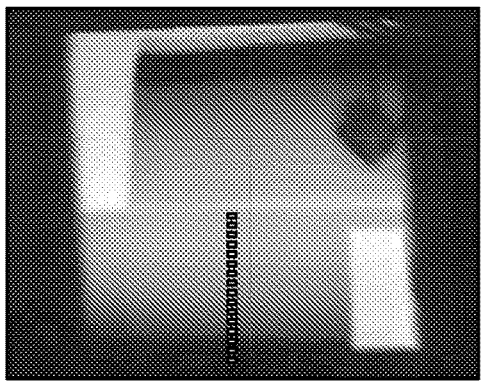
Figure 9B:
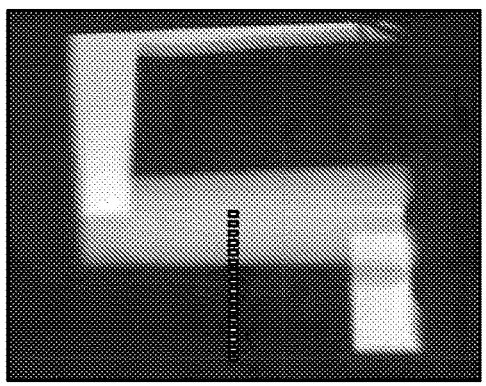
Figure 9E:
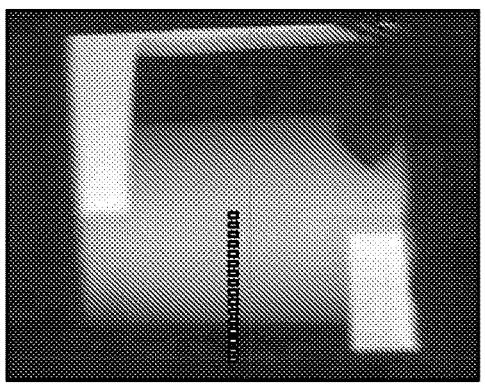
Figure 9A:
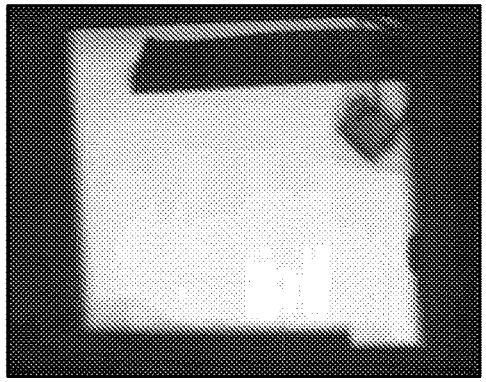
Figure 9D:
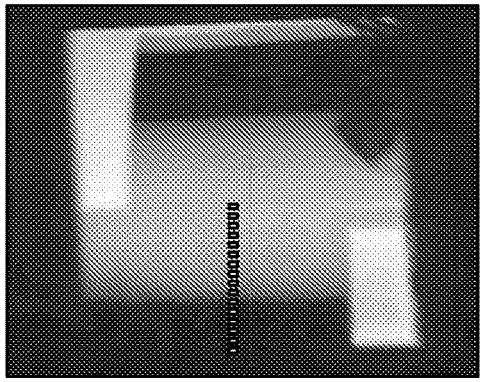
Figure 10:
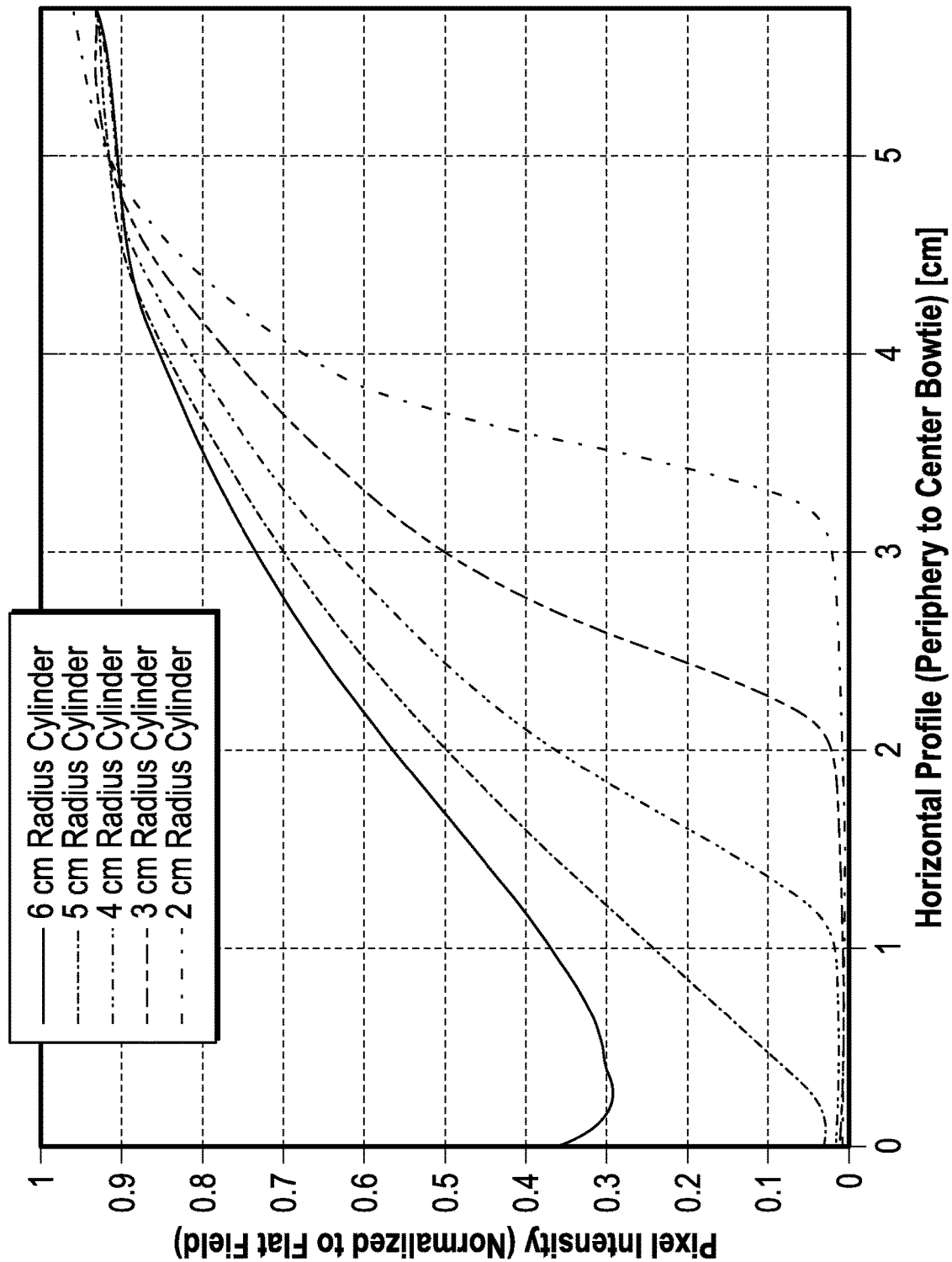
FIG. 10 is a graph showing received radiation intensity profiles for the five different sized cylindrical objects of FIGS. 9B-9F at the marked locations.

In a first experiment, x-ray flood-field images of the filter compensating for the expected attenuation of cylinders with radii 2, 3, 4, 5 and 6 cm were acquired. The images, shown in FIGS. 9A-9F, demonstrate that the adaptive filter can modulate the x-ray beam fluence in a similar way as a traditional attenuating bow-tie for different object diameters. FIG. 10 shows five line profiles taken at the center of the flood-field images of FIGS. 9B-9F, normalized by the profile with the static, open collimators of FIG. 9A. The line profiles show the smooth modulation of the x-ray fluence for the five different sized cylinders generated by the motion of the dynamic collimators.

Figure 11A:
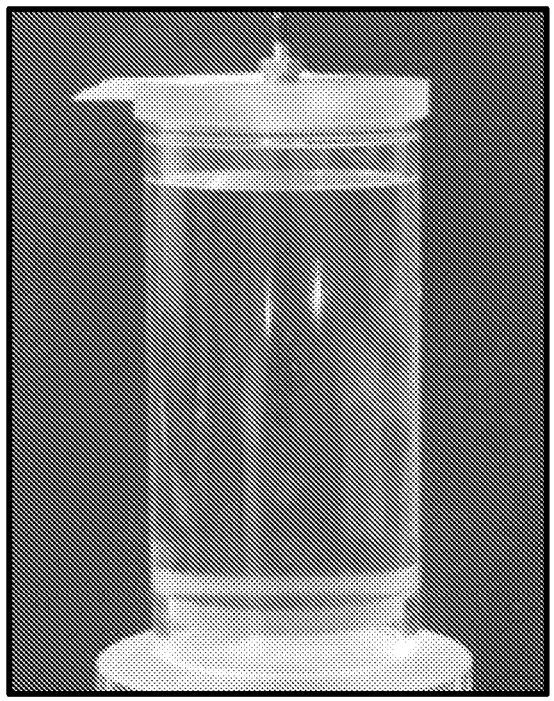
FIG. 11A shows an exemplary cylindrical object used in a validation test.
Figure 11B:
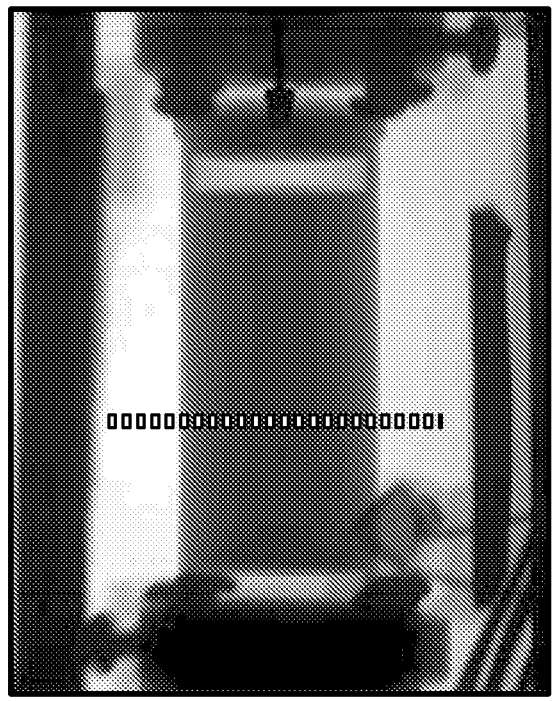
FIG. 11B is a radiograph of the object shown in FIG. 11A with the adaptive filter open.
Figure 11C:
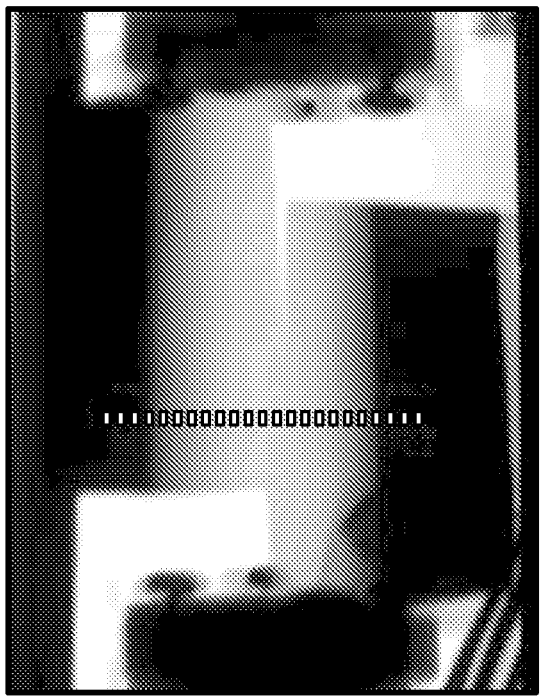
FIG. 11C is a radiograph showing the adaptive filter flood field alone without the cylindrical object.
Figure 11D:
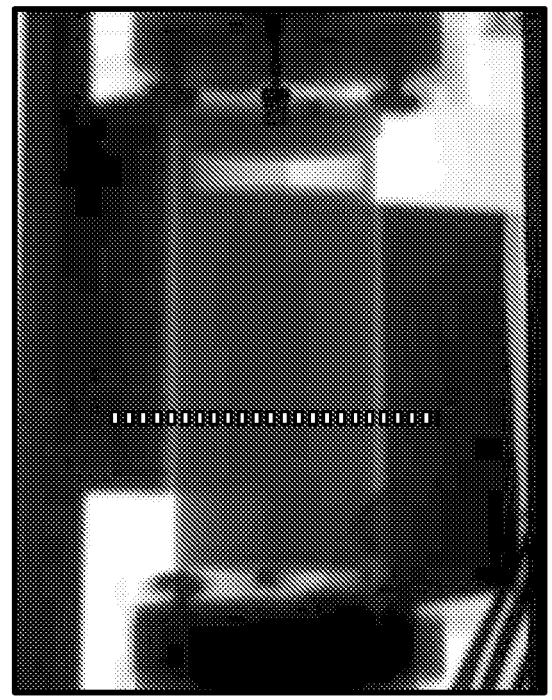
FIG. 11D is a radiograph showing the adaptive filter and the cylindrical object together.
Figure 12:
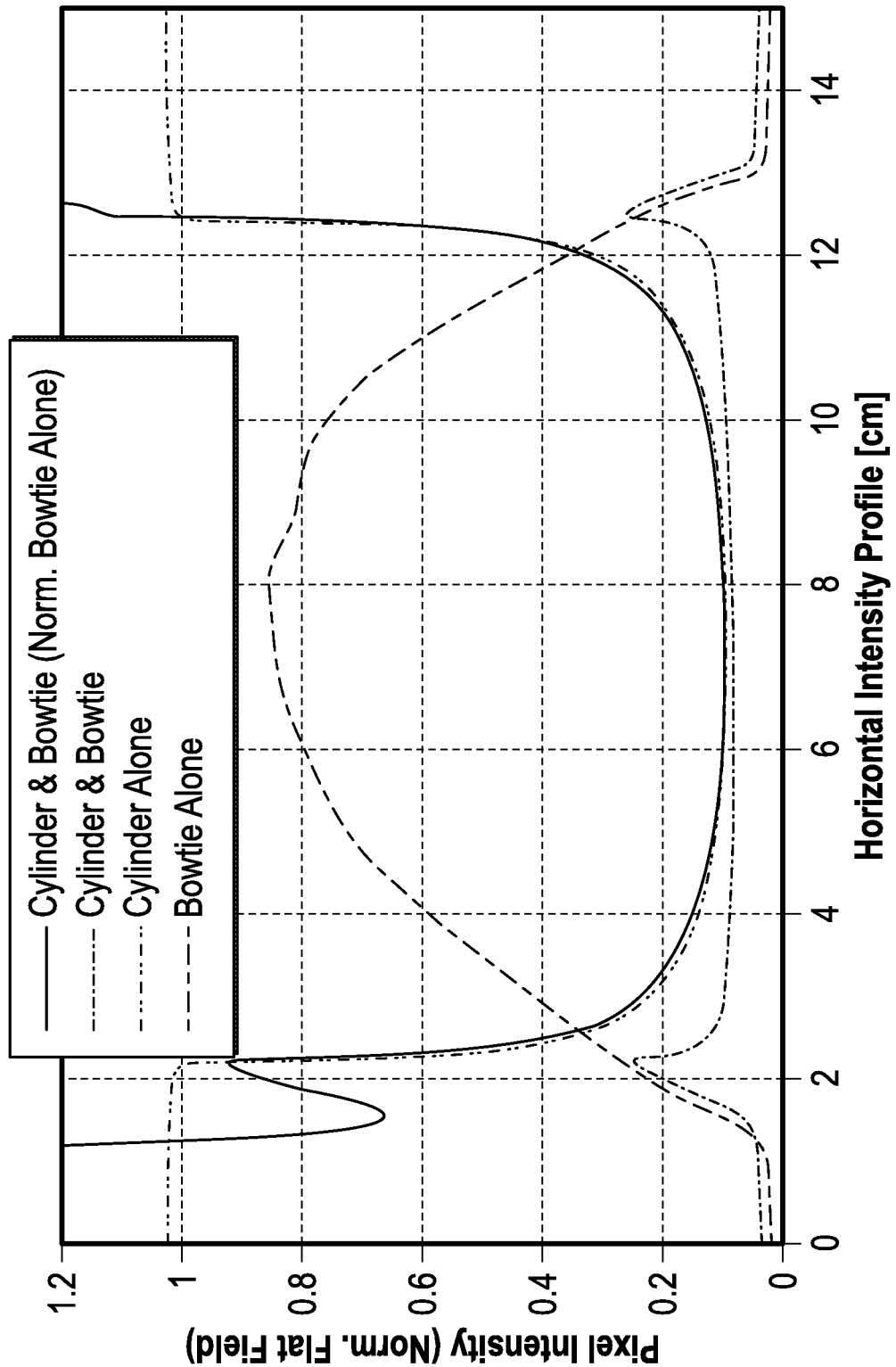
FIG. 12 is a graph showing received radiation intensity profiles for the configurations of FIGS. 11B-11D at the marked locations.

In a second experiment, images of the adaptive filter compensating for a 5 cm radius cylinder composed of a liquid mixture equivalent to 60% adipose, 40% glandular breast tissue were acquired. FIG. 11A shows the imaged object and FIGS. 11B-11D show corresponding x-ray projections. FIG. 11B shows the x-ray projection with just the cylinder object and no filter. FIG. 11C shows the x-ray projection with just the adaptive filter and without the cylinder object. FIG. 11D shows the x-ray profile with both the cylinder object and the adaptive filter. FIG. 12 presents the line profiles at the center of the projections. The flat intensity profile obtained when imaging the cylinder object and the adaptive filter together (labeled "Cylinder and bowtie") demonstrates that the adaptive filter successfully corrects for the expected attenuation of the cylinder. Dividing this profile by the adaptive filter flood-field profile, the original cylinder profile is recovered, as expected. With the adaptive filter, the sufficient detector dynamic range can be substantially smaller (e.g., maximum pixel intensity 20% of the original maximum intensity), which can be useful to prevent saturation and pile-up in photon counter detectors, the dose to the object can be lower, and the pixel variance in the image can be substantially constant (due to an almost constant intensity detected in substantially every pixel inside the object projection). The adaptive filter can also block irrelevant radiation outside the object to limit the saturation of the detector, and reduce the amount of scatter and veiling glare. Alternative driving mechanisms, such as voice-coil actuators, can also be used to provide the different speed and repeatability characteristics of the device motion.

Figure 13:
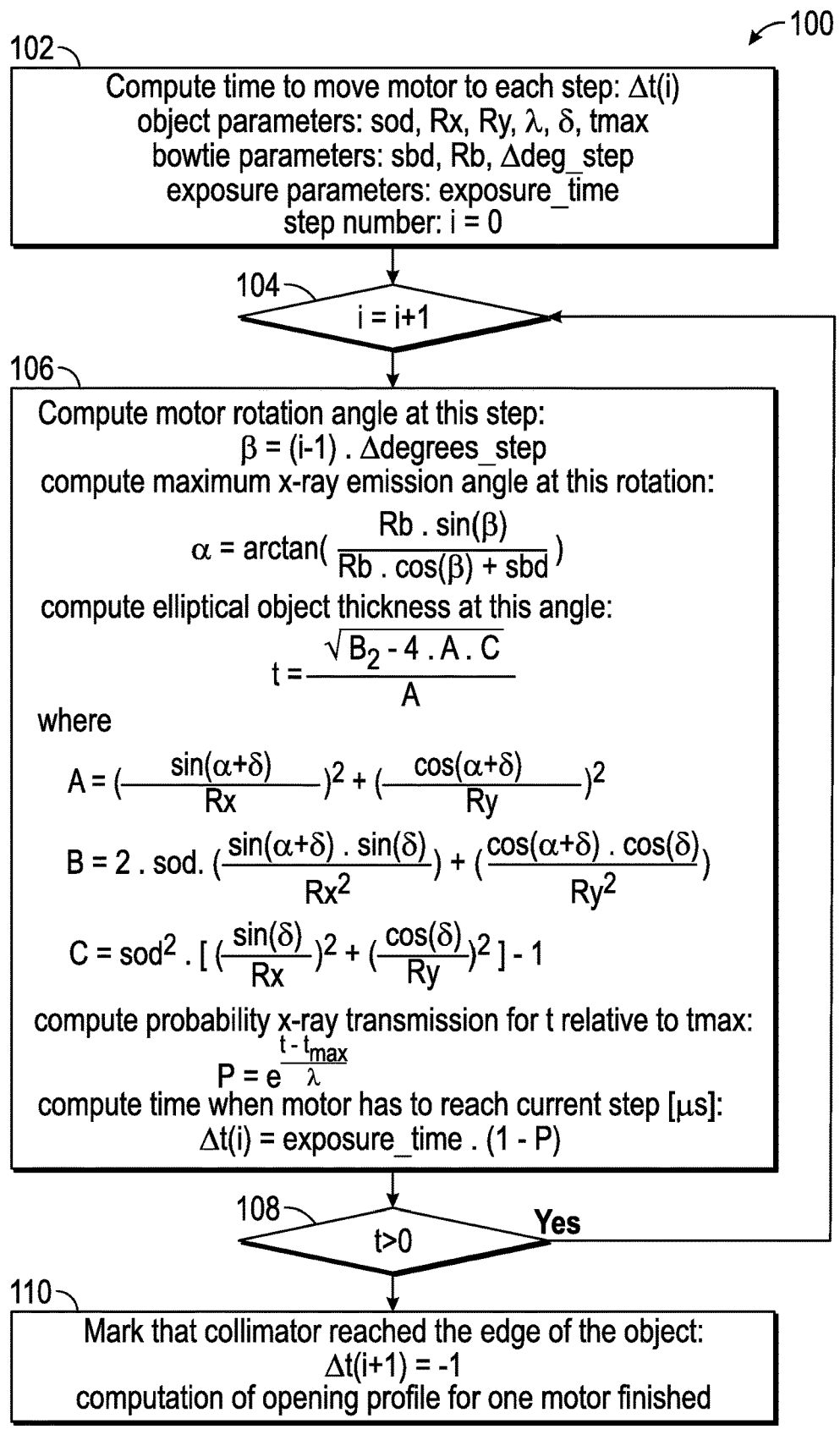
FIGS. 13 and 14 are flowcharts illustrating exemplary methods disclosed herein.

FIG. 13 is a flow chart 100 illustrating an exemplary algorithm for computing/determining an opening movement profile for one of the collimator motors for an exemplary embodiment of the disclosed x-ray system shown in FIG. 1B. At 102, the controller determines a time to move the motor to each step along a full opening movement profile (starting from a closed position) during a single exposure, using various input parameters derived from the geometry of the system set up, the geometry of the object, radiation exposure timing parameters, etc. At 104, the algorithm is advanced to the next iteration corresponding to each step along the opening movement profile. At 106, the controller computes various angles, probabilities, times, and other values that determine the amount of time that the motor has to wait before advancing to the next step, based on the input parameters and times determined at 102 and/or other factors. At 108, the algorithm determines if the thickness of the object at the given step angle is greater than 0 or not, and if so, it returns to 104 to compute the next iteration for the next step. Otherwise, at 110, the controller marks that the collimator has reached the edge of the object, in which case the computation of the opening profile for that motor is complete. The same process can be performed for the other motor. The algorithm 100 can be used to calculate the exact time at which each motor has to advance one step to compensate for the attenuation of the exemplary elliptical object shown in FIG. 1B. The movement profile can be computed independently for each one of the motors, and can be re-calculated whenever the object orientation changes (e.g., for each projection in a computed tomography scan). An equivalent algorithm can be used to compute the movement profile in the opposite direction to close the collimators from a starting open position, or to successively open and close the collimators during the exposure to finish the movement back at the starting position.

Figure 14:
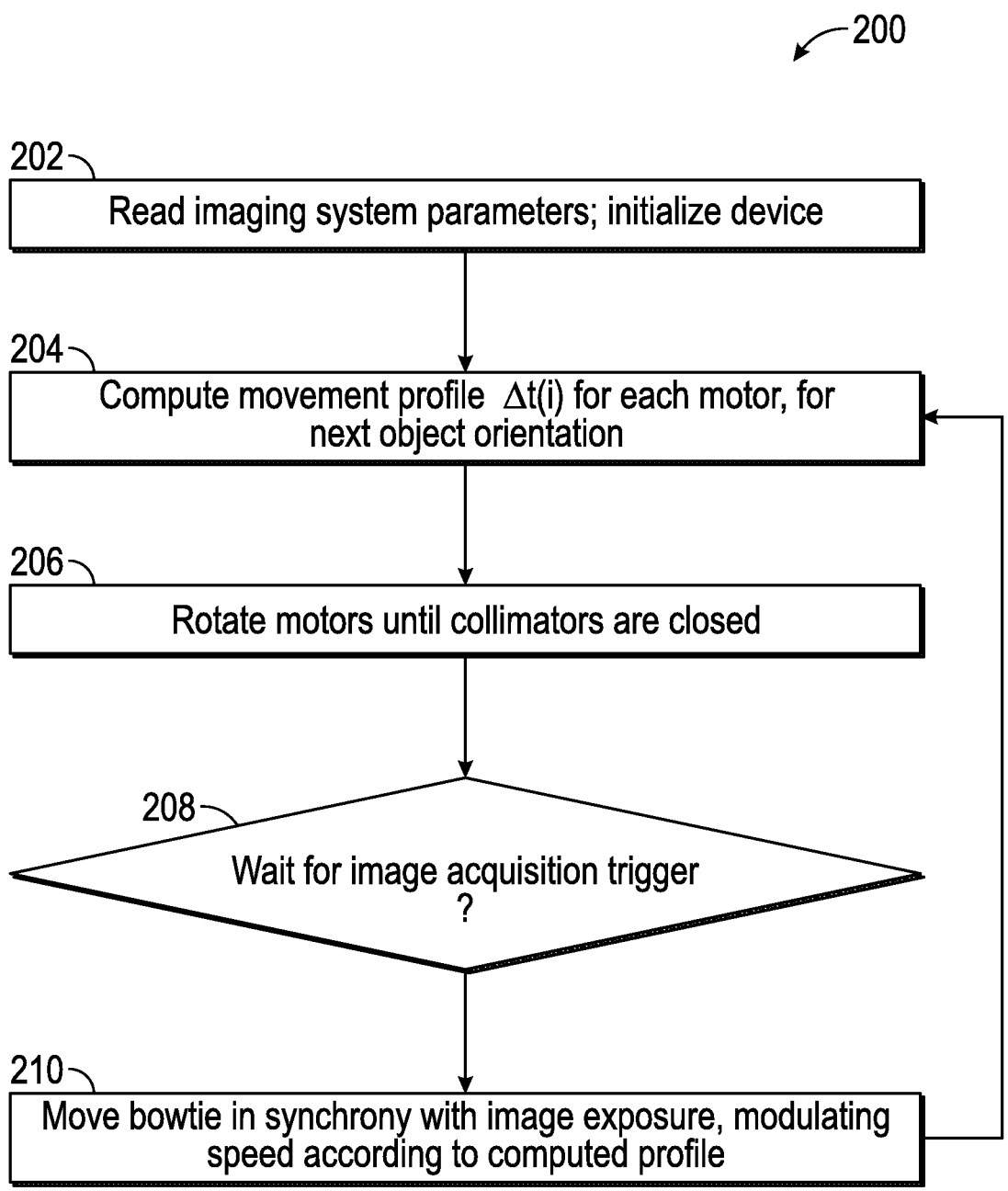

FIG. 14 is a flow chart 200 illustrating a general algorithm for controlling a radiological imaging system including an adaptive filter as disclosed herein in a typical computed tomography or tomosynthesis application in which multiple images are acquired at different orientations. At 202, the controller reads imaging system parameters and initializes the adaptive filter. At 204, the controller computes the movement profile for each motor for the next object orientation. This step 204 can be performed, for example, by using the algorithm 100 shown in FIG. 13 for each motor. At 206, the motors are rotated until the collimators are closed, if not already. At 208, the system waits for an image acquisition trigger indicating the radiation source is ready to emit radiation for the current object orientation. At 210, the controller moves the adaptive filter in synchrony with the radiation exposure, modulating the speed and position of the collimators according to the computed movement profile during the radiation exposure for that object orientation. This process can then be repeated for each exposure at another object orientation. The movement profiles of each collimator can be actively monitored/audited and/or adjusted if needed during an exposure using a feedback loop that includes position encoders/sensors coupled to the collimators to determine the exact current position of each collimator in live time. Data including the input parameters, system geometry, object shape and other properties, the computed collimator movement profiles, and/or other information can be stored in a database, memory, and/or other data storage system for future use and/or analysis.

The adaptive filter 14 can move quickly between each step in a collimator movement profile to provide a smoother, more accurate and effective filtering result. In some embodiments, each collimator moves through at least 30 steps from closed to fully open positions. Each step can be less than 1°, for example. In one example, the opening movement profile for a collimator has 32 sub-steps for each full-step of 0.8°. The entire opening motion (e.g., about 30° divided in 1200 sub-steps) can take 25.0 millisecond or less in some embodiments. In one example, each step takes 20 microseconds or less. In other examples, each step takes 10 microseconds or less. Shorter steps can take less time, and thus including more, shorter steps to achieve the entire opening motion can be desirable. In still other embodiments, the collimators can move in a continuous, analog motion that does not include discrete steps, or can comprise a great many, or substantially infinite, number of very small steps.

The disclosed adaptive filter and related systems and methods provide for spatial exposure-time modulation as a means for radiation beam shaping. Other known static or adaptive bow-tie filters are based on the idea of differentially attenuating the intensity of the radiation beam using partially radio-opaque components with a particular shape (e.g., wedges, cylinders). Contrarily, the disclosed technology uses collimators that typically block 100% of the incoming radiation, though some embodiments may block less than 100% of the radiation. The intensity modulation is therefore not produced by a differential attenuation but by a precise timing of the transmission and blocking of the radiation field at different emission angles. Some of the alternative adaptive bow-tie filters and region-of-interest collimators move between discrete exposures of a computed tomography acquisition, but remain static during each radiation exposure. The operation of the disclosed device has to be synchronized with the emission of the radiation from the source using a controller in signal communications with the computerized imaging system.

In the fields of photography and radiation therapy there are devices that use moving radiation blockers, such as focal-plane shutters and multi-leaf collimators. However, a unique characteristic of the disclosed technology is that the adaptive filter does not simply translate the collimators at a fixed speed to open or close a field of view, but instead actively modulates the speed and acceleration of the collimator to produce a pre-computed exposure time distribution. Furthermore, an aim of the disclosed technology is to homogenize the radiation arriving at the detector, as opposed to other filter technologies that aim to modulate the dose distribution inside the patient (as it is the case in radiotherapy).

Additional advantages of the disclosed technology with respect to static bow-tie filters can include adaptability to patient size, patient off-center position, x-ray energy variation, patient geometric distance variation, and source rotation angle variation relative to the patient. Compared to other dynamic bow-tie designs, the disclosed technology can be adapted to any patient size and patient location inside the imaging system, reduce or eliminate scatter contamination coming from the device, and can produce more flexible and smoother profiles than those that can be generated by filters using discrete attenuating wedges.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. I therefore claim at least all that comes within the scope of these claims.

The invention claimed is:

1. An apparatus for modifying a radiation beam between a radiation source and a radiation detector, based on an object to be imaged using the radiation beam, the apparatus comprising:
at least one collimator that attenuates radiation that is incident upon the collimator; and
at least one motor operable to move the collimator, during a single continuous radiation exposure that is detected by the radiation detector, along a predefined path relative to a radiation axis defined by the direction that radiation travels from the radiation source to through the object to be imaged and to the radiation detector;
wherein the apparatus has a closed position wherein the collimator blocks the radiation axis so that no portion of a radiation beam from the radiation source can pass by the collimator to reach the object;
wherein the motor is operable to move the collimator along the predefined path between the closed position and a plurality of open positions, either continuously or by discrete steps, during the single continuous radiation exposure, wherein in each open position a different portion of the object is exposed to radiation from the radiation source passing by the collimator and detected by the radiation detector; and
wherein the motor is synchronized with an exposure start time and an exposure end time of the radiation source, the start time and end time being fora the single continuous radiation exposure, such that the motion of the collimator permits varying amounts of radiation from the radiation source to reach each portion of the object during the single continuous radiation exposure, wherein the varying amounts of radiation are based at least in part on a shape of the object and an orientation of the object relative to the radiation source.

2. The apparatus of claim 1, wherein the at least one collimator blocks substantially all radiation that is incident upon the at least one collimator from the radiation source.

3. The apparatus of claim 1, wherein the at least one collimator allows a substantial portion of the radiation that is incident upon at least one collimator from the radiation source to pass by the at least one collimator and reach the target, wherein the material and thickness of the at least one collimator are selected to attenuate a specific amount of the radiation.

4. The apparatus of claim 1, wherein the at least one collimator comprises first and second collimators, and wherein the first and second collimators have opposing edges that are adjacent to each other in the closed position, and the opposing edges are straight and parallel.

5. The apparatus of claim 1, wherein the at least one collimator comprises first and second collimators, and wherein the first and second collimators have opposing edges that are adjacent to each other in the closed position, and the opposing edges are curved.

6. The apparatus of claim 1, wherein the at least one collimator comprises first and second collimators, and wherein:
the at least one motor is operable to move the first and second collimators apart from each other along the predefined paths from the closed position to the plurality of increasingly spaced apart open positions, wherein in each open position an increasingly greater portion of the radiation beam from the radiation source is permitted to pass through the apparatus between the first and second collimators to the object; or the at least one motor is operable to move the first and second collimators toward each other along the predefined paths from an initial open position to a plurality of decreasingly spaced apart open positions, wherein in each successive open position a decreasingly lesser portion of the radiation beam from the radiation source is permitted to pass through the apparatus between the first and second collimators to the object.

7. The apparatus of claim 1, wherein the at least one collimator moves along a predefined curved path about a pivot axis, the pivot axis being transverse to the radiation axis.

8. The apparatus of claim 7, wherein the at least one collimator comprises a curved plate, such that a major surface of the plate has a curvature centered on the pivot axis of the collimator.

9. The apparatus of claim 1, wherein the at least one collimator moves along a predefined linear path that is transverse to the radiation axis.

10. A method for controlling radiation exposure across a target object during a radiographic imaging exposure, the method comprising:

positioning an adaptive filter between a radiation source and a radiation detector with a target object being between the adaptive filter and the radiation detector, wherein the adaptive filter comprises at least one collimator that attenuates radiation that is incident upon the collimator; and moving the at least one collimator during a single continuous radiation emission from the radiation source and detected by the radiation detector, such that the motion of the at least one collimator allows different amounts of radiation from the radiation source to pass by the at least one collimator to each portion of the target object during the single continuous radiation emission, wherein the different amounts of radiation allowed to reach each portion of the target object are based at least in part on a shape of the target object and an orientation of the target object relative to the radiation source and the adaptive filter;

wherein the at least one collimator begins to move at a first predetermined time after the radiation source begins to emit radiation toward the target object during the single continuous radiation emission, and the at least one collimator reaches a maximum movement distance at a second predetermined time before the radiation source stops emitting radiation toward the target object that is detected by the radiation detector.

11. The method of claim 10, wherein moving the at least one collimator comprises pivoting the at least one collimator along a curved path about a common pivot axis, the common pivot axis being transverse to an axis of the radiation emission.

12. The method of claim 10, wherein the method comprises generating a movement profile for the at least one collimator, wherein the movement profile is based on a cross-sectional shape of the target object and the orientation of the target object relative to the radiation source and the adaptive filter.

13. The method of claim 12, wherein the movement profile is also based on a radius from a pivot axis of the adaptive filter to the at least one collimator.

14. The method of claim 12, wherein the movement profile causes the target object to receive a radiation exposure profile across a width of the target object that is generally proportional to a thickness profile of the target object across the width of the target object.

15. The method of claim 10, wherein moving the at least one collimator comprises moving the at least one collimator in a plurality of small steps such that the at least one collimator stops or slows briefly between each step.

16. The method of claim 15, wherein the plurality of small step comprises at least 30 steps, or the at least one collimator stops for 1 millisecond or less between each step, or the at least collimator pivots 1° or less between each successive step.

17. The method of claim 10, further comprising combining an image acquired from the radiographic imaging procedure with the adaptive filter and a target object with a reference image acquired with the same adaptive filter motion but without the object to produce an image that looks like a raw radiographic image that would have been produced under the same imaging circumstances if the adaptive filter was not present in the imaging system.

18. The method of claim 10, wherein the single continuous radiation emission is one of a plurality of sequential radiation emissions targeting the target object during a radiographic imaging procedure;

wherein the plurality of sequential radiation emissions are temporally separated by brief non-radiation periods with no radiation emission, during which the radiation source, the target object, or both, are moved or adjusted; and wherein during each of the plurality of sequential radiation emissions, the at least one collimator begins to move at a first predetermined time after the radiation source begins to emit radiation toward the target object, and the at least one collimator reaches a maximum movement distance at a second predetermined time before the radiation source stops emitting radiation toward the target object.

19. The method of claim 10, wherein the at least one collimator comprises first and second collimators, and wherein moving the at least one collimator comprises moving the first and second collimators apart from or toward each other by moving the first and second collimators in opposite directions along linear paths transverse to an axis of the radiation emission.

20. A system comprising:
a radiation source;
a radiation detector; and
an adaptive filter positioned between the radiation source and the radiation detector, wherein the adaptive filter comprises first and second collimators that attenuate radiation that is incident upon the collimators;

wherein the system is configured to include a target object positioned between the adaptive filter and the radiation detector such that the target object can be radiologically imaged; and wherein the system is operable to move the first and second collimators apart from or toward each other during a single continuous radiation emission from the radiation source that is detected by the radiation detector, such that the motion of the collimators allows different amounts of radiation from the radiation source to pass between the two collimators to each portion of the target object during the single continuous radiation emission, wherein the different amounts of radiation allowed to reach each portion of the target object are determined based on a thickness of each portion of the target object, as measured in the direction the radiation travels, such that the radiation detector receives a more uniform distribution of radiation through the target object.

21. The system of claim 20, wherein the system is operable to move the first and second collimators apart from or toward each other in opposite directions along curved paths about a common pivot axis.

22. The system of claim 20, wherein the first and second collimators begin to move apart from or toward each other at a predetermined time after the radiation source begins to emit radiation toward the target object, and the first and second collimators reach a maximum or minimum separation from each other at a predetermined time before the radiation source stops emitting radiation toward the target object.

* * * * *